(12) United States Patent
Lal et al.

(10) Patent No.: US 6,235,715 B1
(45) Date of Patent: May 22, 2001

(54) HUMAN MEMBRANE RECYCLING PROTEINS

(75) Inventors: Preeti Lal, Santa Clara; Purvi Shah, Sunnyvale; Neil C. Corley, Mountain View, all of CA (US)

(73) Assignee: Incyte Pharmaceuticals, Inc., Palo Alto, CA (US)

( * ) Notice: Subject to any disclaimer, the term of this patent is extended or adjusted under 35 U.S.C. 154(b) by 0 days.

(21) Appl. No.: 09/360,125

(22) Filed: Jul. 23, 1999

Related U.S. Application Data

(62) Division of application No. 09/004,502, filed on Jan. 8, 1998, now Pat. No. 5,962,263.

(51) Int. Cl.$^7$ .................................................. C07K 14/00
(52) U.S. Cl. .............................. 514/12; 530/300; 530/350
(58) Field of Search ................................... 530/350, 300; 514/12

(56) References Cited

PUBLICATIONS

Winfield et al. (Oct. 1997; Genome Res. 7:1020–1026).*
Sudhof, T.C. and Jahn, R. "Proteins of Synaptic Vesicles Involved in Exocytosis and Membrane Recycling" *Neuron* (1991) 6:665–677.
Sudhof, T.C. et al., "Membrane Fusion Machinery: Insights from Synaptic Proteins" *Cells* (1993) 75:1–4.
Brand, S.H. et al., "Secretory Carrier Membrane Proteins 31–35 Define a Common Protein Composition among Secretory Carrier Membranes" *J.Biol.Chem.* (1991) 266:18949–18957.
Brand, S.H. and Castle, J.D. "SCAMP 37, a new marker within the general cell surface recycling system" *EMBO J.* (1993) 12:3753–3761.
Laurie, S.M. et al., "The Glucose Transporter GluT4 and Secretory Carrier Membrane Proteins (SCAMPs) Colocalize in Rat Adipocytes and Partially Segregate during Insulin Stimulation" *J.Biol.Chem.* (1993) 25:19110–19117.
Brand, S.H. and Castle, J.D. (GI 487057), GenBank Sequence Database (Accession S37395), National Center for Biotechnology Information, National Library of Medicine, Bethesda, Maryland, 20894.
Wu, T.T. and Castle, J.D. "Evidence for colocalization and interaction between 37 and 39 kDa isoforms of secretory carrier membrane proteins (SCAMPs)" *J.Cell Science* (1997) 110:1533–1541.
Singleton, D.R. et al., (GI 2232243) GenBank Sequence Database (Accession AF05039), National Center for Biotechnology Information, National Library of Medicine, Bethesda, Maryland, 20894.
Singleton, D.R. et al. (GI 2232241) GenBank Sequence Database (Accession AF005038), National Center for Biotechnology Information, National Library of Medicine, Bethesda, Maryland, 20894.
Singleton, D.R. et al., "Three mammalian SCAMPs (secretory carrier membrane proteins) are highly related proteins of distinct genes having similar subcellular distributions" *J.Cell Science* (1997) 110:2099–2107.

* cited by examiner

*Primary Examiner*—Karen Cochrane Carlson
(74) *Attorney, Agent, or Firm*—Incyte Genomics, Inc.

(57) ABSTRACT

The invention provides human membrane recycling proteins (HMRP) and polynucleotides which identify and encode HMRP. The invention also provides expression vectors, host cells, antibodies, agonists, and antagonists. The invention also provides methods for treating or preventing disorders associated with expression of HMRP.

2 Claims, 12 Drawing Sheets

```
5' NGA CGC AGG CGC AAC CCA CGG CTG CTG GGA TCC TTG TGG CCC TTC CGG TCG
                9          18          27          36          45          54

ATG GAA CCA ATC CGT GCA CAG AGA AGC GGG GCG AAC TGA GGC GAG TGA AGT GGA
                63          72          81          90          99         108

CTC TGA GGG CTA CCG CCA CTA CCG CTG CGG GGG CAG GGG CAG AGG
                117         126         135         144         153         162

GCC GAG GCC GCA GTT GCA AAC ATG GCT CAG AGC AGA GAC GGC GGA AAC CCG
                171         180         189         198         207         216
                         M   A   Q   S   R   D   G   G   N   P

TTC GCC GAG CCC AGC GAG CTT GAC AAC CCC TTT CAG GAC CCA GCT GTG ATC CAG
    F   A   E   P   S   E   L   D   N   P   F   Q   D   P   A   V   I   Q
                225         234         243         252         261         270

CAC CGA CCC AGC CGG CAG TAT GCC ACG CTT GAC GTC TAC AAC CCT TTT GAG ACC
    H   R   P   S   R   Q   Y   A   T   L   D   V   Y   N   P   F   E   T
                279         288         297         306         315         324

CGG GAG CCA CCA CCA TAT GAG CCT CCA GCC CCT GCC CCA TTG CCT CCA CCC
    R   E   P   P   P   Y   E   P   P   A   P   A   P   L   P   P   P
                333         342         351         360         369         378

TCA GCT CCC TCC TTG CAG CCC TCG AGA AAG CTC AGC CCC ACA GAA CCT AAG AAC
    S   A   P   S   L   Q   P   S   R   K   L   S   P   T   E   P   K   N
                387         396         405         414         423         432
```

FIGURE 1A

```
     441             450         459         468         477         486
TAT  GGC  TCA  TAC  AGC  ACT  CAG  GCC  TCA  GCT  GCA  GCC  ACA  GCT  GAG  CTG
 Y    G    S    Y    S    T    Q    A    S    A    A    A    T    A    E    L 495             504         513         522         531         540
AAG  AAA  CAG  GAG  GAG  CTC  AAC  CGG  AAG  GCA  GAG  TTG  GAC  CGA  AGG  CGA
 K    K    Q    E    E    L    N    R    K    A    E    L    D    R    R    R 549             558         567         576         585         594
GAG  CTG  CAG  CAT  GCT  GCC  CTG  GGG  ACA  GCT  ACT  CGA  CAG  AAC  AAT  TGG  CCC
 E    L    Q    H    A    A    L    G    T    A    T    R    Q    N    N    W    P 603             612         621         630         639         648
CCT  CTA  TCT  TTT  TGT  CCA  GTT  CAG  CCC  TGC  TTT  TTC  CAG  GAC  ATC  TCC  ATG
 P    L    S    F    C    P    V    Q    P    C    F    F    Q    D    I    S    M 657             666         675         684         693         702
GAG  ATC  CCC  CAA  GAA  TTT  CAG  AAG  ACT  GTA  TCC  ACC  ATG  TAC  CTC  TGG  ATG
 E    I    P    Q    E    F    Q    K    T    V    S    T    M    Y    L    W    M 711             720         729         738         747         756
TGC  AGC  ACG  CTG  GCT  CTT  CTC  CTG  AAC  TTC  CTC  GCC  TGC  CTG  AGC  TTC  TGT
 C    S    T    L    A    L    L    L    N    F    L    A    C    L    S    F    C 765             774         783         792         801         810
GTG  GAA  ACC  AAC  AAT  GGC  GCA  GGC  TTT  GGG  CTT  TCT  ATC  CTC  TGG  GTC  CTC  CTT
 V    E    T    N    N    G    A    G    F    G    L    S    I    L    W    V    L    L
```

FIGURE 1B

```
      819         828         837         846         855         864
TTC ACT CCC TGC TCC TTT GTC TGC TGG TAC CGC CCC ATG TAT AAG GCT TTC CGG
 F   T   P   C   S   F   V   C   W   Y   R   P   M   Y   K   A   F   R
      873         882         891         900         909         918
AGT GAC AGT TCA TTC AAT TTC GTT TTC TTC ATT TTC TTC GTC CAG GAT
 S   D   S   S   F   N   F   V   F   F   I   F   F   V   Q   D
      927         936         945         954         963         972
GTG CTT GTC CTC CAG GCC ATT GGT ATC CCA GGT TGG GGA TTC AGT GGC TGG
 V   L   V   L   Q   A   I   G   I   P   G   W   G   F   S   G   W
      981         990         999        1008        1017        1026
ATC TCT GCT CTG GTG CCG AAG AAC ACA GCA GTA TCC GTG CTC ATG CTG
 I   S   A   L   V   P   K   N   T   A   V   S   V   L   M   L
     1035        1044        1053        1062        1071        1080
CTG GTC GCC CTG CTC TTC ACT GGC ATT GCT GTG CTA GGA ATT GTC ATC CTG AAA
 L   V   A   L   L   F   T   G   I   A   V   L   G   I   V   I   L   K
     1089        1098        1107        1116        1125        1134
CGG ATC CAC TCC TTA TAC CGC CGC TTC ACA GGT GCC TTT CAG AAG GCC CAG CAA
 R   I   H   S   L   Y   R   R   F   T   G   A   S   F   Q   K   A   Q   Q
     1143        1152        1161        1170        1179        1188
GAA TTT GCT GCT GGT GTC TTC TCC AAC CCT GCG GTG CGA ACC GCA GCT GCC AAT
 E   F   A   A   G   V   F   S   N   P   A   V   R   T   A   A   A   N
```

FIGURE 1C

```
     1197          1206          1215          1224          1233          1242
GCA GCC GCT GGG GCT GCT GAA AAT GCC TTC CGG GCC CCG TGA CCC CTG ACT GGG
 A   A   A   G   A   A   E   N   A   F   R   A   P 1251          1260          1269          1278          1287          1296
ATG CCC TGG CCC TGC TAC TTG AGG GAG CTG ACT TAG CTC CCG TCC CTA AGG TCT 1305          1314          1323          1332          1341          1350
CTG GGA CTT GGA GAG ACA TCA CTA ACT GAT GGC TCC TCC GTA GTG CTC CCA ATC 1359          1368          1377          1386          1395          1404
CTA TGG CCA TGA CTG AAC CTG ACA GGC GTG TGG GGA GTT CAC TGT GAC CTA 1413          1422          1431          1440          1449          1458
GTC CCC CCA TCA GGC CAC ACT GCT GCC ACC TCT CAC ACG CCC CAA CCC AGC TTC 1467          1476          1485          1494          1503          1512
CCT CTG CTG TGC CAC GGC TGT TGC TTC GGT TAT TTA AAT AAA AAG AAA GTG GAA

1521
CTG GAA CTG 3'
```

FIGURE 1D

```
5' NCC GGA AGT GGA GGG TCT ACA CGA AGC GCC GCT GGG TCT GGG TGC CCG GAG GCA
                 9              18              27              36              45              54

GCA GCG TTC GCG GAG TTC GCC CGC CGG CCC CCG ATC ACC ATG TCG GCT TTC GAC
                 63              72              81              90              99              108
                                                              M   S   A   F   D

ACC AAC CCC TTC GCG GAC CCA GTG GAT GTA AAC CCC TTC CAG GAT CCC TCT GTG
    T   N   P   F   A   D   P   V   D   V   N   P   F   Q   D   P   S   V
                 117             126             135             144             153             162

ACC CAG ACC AAC GCC CCG CAG GGC GGG CTG GCG GAA TTC CCC TTC TCA
    T   Q   T   N   A   P   Q   G   G   L   A   E   F   P   F   S
                 171             180             189             198             207             216

GAG ACA AAT GCA GCG ACA ACA GTT CCT GTC ACC CAA CTC CCT GGG TCC TCA CAG
    E   T   N   A   A   T   T   V   P   V   T   Q   L   P   G   S   S   Q
                 225             234             243             252             261             270

CCA GCG GTT CTC CAG GAA CCA TCA GTG CAG CCG ACC CCC CAG GCC GTG
    P   A   V   L   Q   E   P   S   V   Q   P   T   P   Q   A   V
                 279             288             297             306             315             324

GTG TCT GCA GCC CAG GGC CTG CTC CGG CAG CAG GAA GAA GAA CTG GAC AGG AAA
    V   S   A   A   Q   G   L   L   R   Q   Q   E   E   E   L   D   R   K
                 333             342             351             360             369             378
```

FIGURE 2A

```
GCT GCC GAG CTG GAA CGC AAG GAG GAG CTG CAG AAC ACT GTA GCC AAC TTG
 A   A   E   L   E   R   K   E   E   L   Q   N   T   V   A   N   L
387     396     405     414     423     432

CAT GTG AGA CAG AAC TGG CCC CTG CCC TCG TGG TGC CCT GTG AAG CCC
 H   V   R   Q   N   W   P   L   P   S   W   C   P   V   K   P
441     450     459     468     477     486

TGC TTC TAT CAG GAT TTC TCC ACA GAG ATC CCT GCC GAC TAC CAG CGG ATA TGC
 C   F   Y   Q   D   F   S   T   E   I   P   A   D   Y   Q   R   I   C
495     504     513     522     531     540

AAG ATG CTC TAC TAT CTG TGG ATG TTG CAT TCA GTG ACT CTG TTT CTG AAC CTG
 K   M   L   Y   Y   L   W   M   L   H   S   V   T   L   F   L   N   L
549     558     567     576     585     594

CTT GCC TGC CTG TGG GCC AAC AGC TCC ACT CCC TGT GCC TTC AAG GGA GTG GAC TTT GGC
 L   A   C   L   W   A   N   S   S   T   P   C   A   F   K   G   V   D   F   G
603     612     621     630     639     648

CTC TCC ATC TAC AAG TTT CTG ATC TTC ACT CCC TGT GCC TTC TGT TGG TAC
 L   S   I   Y   K   F   L   I   F   T   P   C   A   F   C   W   Y
657     666     675     684     693     702

CGA CCC ATC TAT AAG GCC TTT AGG TCC GAC AAC TCT TTC AGC TTC GTG TTC
 R   P   I   Y   K   A   F   R   S   D   N   S   F   S   F   V   F
711     720     729     738     747     756
```

FIGURE 2B

```
       765       774       783       792       801       810
TTC TTT TTT TTT TGT CAA ATA GGG ATC TAC ATC CAG TTG GTT GGC ATC
 F   F   F   F   C   Q   I   G   I   Y   I   Q   L   V   G   I
       819       828       837       846       855       864
CCT GGC CTG GGG GAC AGC GGT TGG ATT GCA GCC CTG TCT ACA GAT AAT CAT
 P   G   L   G   D   S   G   W   I   A   A   L   S   T   D   N   H
       873       882       891       900       909       918
TCC CTG GCC ATA TCA GTC ATC ATG GTG GTG GCT GGC TTC TTC ACC CTC TGT
 S   L   A   I   S   V   I   M   V   V   A   G   F   F   T   L   C
       927       936       945       954       963       972
GCC GTG CTC TCA GTC TTC CTC CTG CAG CGG GTG CAC TCC TAC CGA CGG ACA
 A   V   L   S   V   F   L   L   Q   R   V   H   S   Y   R   R   T
       981       990       999      1008      1017      1026
GGG GCC AGC TTC CAG GCC CAG GAG GAG TTT TCC CAG GGC ATC TTC AGC AGC
 G   A   S   F   Q   A   Q   E   E   F   S   Q   G   I   F   S   S
      1035      1044      1053      1062      1071      1080
AGA ACC TTC CAC AGA GCT GCT TCA TCT GCT GCC CAA GGA GCC TTC CAG GGG AAT
 R   T   F   H   R   A   A   S   S   A   A   Q   G   A   F   Q   G   N
      1089      1098      1107      1116      1125      1134
TAG TCC TCT CTT CTC TCC CCC TCA GCC TTT CTC TCG CCT GCC TTC TGA GCT
```

FIGURE 2C

```
      1143              1152              1161              1170              1179              1188
GCA CTT TCC GTG GGT GCC TTA TGT GGT GGT TGT GCC CAG CAC AGA CCT GGC 1197              1206              1215              1224              1233              1242
AGG GTT CTT GCC GTG GCT CTT CCT CCC TCA GCG ACC AGC TCT CCC TGG AAC 1251              1260              1269              1278              1287              1296
GGG AGG GAC AGG GAA TTT TTT CCC CCT CTA TGT ACA AAA AAA AAA GCT CTC 1305              1314              1323              1332              1341              1350
TTT CCT TCT CTG GTG ATG GTT TGG TAG GAT TCT TTT GTC TCT GGA AGC AGT GGG 1359              1368              1377              1386              1395              1404
ACT GAA GTT CTC TTC GTC CTG TGC ACA CAC AGA CAC CCC CAC ACA GTT GGG ATC 1413              1422              1431              1440              1449              1458
ACA GGC TGA CCT GGG CCC ATC CCA GCT GGA GCT TTC TGC CAG GGT CCT GGG CCT 1467              1476              1485              1494              1503              1512
TGA CTC CCC CAC CCT GCA GGC CTG GCC TGA ATC TGG CTT CTT AGA CAC AGC CCA 1521              1530              1539              1548              1557              1566
GTC CTT CCT GCC TGG GCT GGG AAT AAG CCT CTC ACA GGT TCT GGT GGA CAG ATC 1575              1584              1593              1602              1611              1620
TGT TCC CCA CAC TCC AGT GGT CTC CAG GCT CTC CAG GCT CCC AGA GAA GGC TGG TTG CCT
```

FIGURE 2D

```
          1629       1638       1647       1656       1665       1674
CAA GCT CTT CTC TGC CTC ATA AAC GGA TCC AGA GAA GGC TGG TTG CCT TAA GCT 1683       1692       1701       1710       1719       1728
CTT CCC TGC CTC GTG TTC CTG AGA AAC GGA TTA ATA GCC CTT TAT CCC CCT GCA 1737       1746       1755       1764       1773       1782
CCC TCC TGC AGG GGA TGG CAC TTT GAG CCC TCT GGA GCC CTC CCC TTG CTG AGC 1791       1800       1809       1818       1827       1836
CTT ACT CTC TTC AGA CTT TCT GAA TGT ACA GTG CCG TTG GTT GGG ATT TGG GGA 1845       1854       1863       1872       1881       1890
CTG GAA GGG ACC AAG GAC ACT GAC CCC AAG CTG TCC TGC CTA GCG TCC AGC GTC 1899       1908       1917       1926       1935       1944
TTC TAG GAG GGT GGG GTC TGC CTG TCC TGG TGT GGT TGG TTT GGC CCT GTT TGC 1953       1962       1971       1980       1989       1998
TGT GAC TAC CCC CCC TCC CCG AAC CGA GGG ACG GCT GCC TTT GTC TCT GCC 2007       2016       2025       2034       2043       2052
TCA GAT GCC ACC TGC CCC GCC CAT GCT CCC CAT CAG CAG CAG CCA GAC TTT CAG 2061       2070       2079       2088       2097       2106
GAA GGG CAG GAC CAG CCA GTC CAG AAC CGC ATC CCT CAG CAG GGA CTG ATA AGC
```

FIGURE 2E

```
          2115           2124           2133           2142           2151           2160
CAT CTC TCG GAG GGC CCC CTA ATA CCC AGT GGA GTC TGG TTC ACA CCC TGG GGG 2169           2178           2187           2196           2205           2214
GTG TGT CAC TGT GAT GGG ACA CGT AGG AGT CCA CCC TTA AAA CCA GCA CCC TGT 2223           2232           2241           2250           2259           2268
CCC TCG AGG CTG CCG AGT GGG TGT GTG GAC TGG GGT GCC TTC CCA CAA AAC TAG 2277           2286           2295           2304           2313           2322
CCT CCG GCT CTG GGC CCG AGA CAG CCG CAG GCC CCA GCC ACT GAA TGA TAC TGG 2331           2340           2349           2358           2367           2376
CAG CGG CTG GGG TTT TAT GAA CTC CTT TCT GGT ATT TTT TCC CCT CTA TGT ACA 2385           2394           2403           2412           2421           2430
AAT GTA TAT GTT ACG TCT CAA TTT TTG TGC TTA AGT AAA AAT AAA AAC ATT TTC

AGA C 3'
```

HUMAN MEMBRANE RECYCLING PROTEINS

This application is a divisional application of U.S. application Ser. No. 09/004,502, filed Jan. 8, 1998 now U.S. Pat. No. 5,962,263.

FIELD OF THE INVENTION

This invention relates to nucleic acid and amino acid sequences of human membrane recycling proteins, and to the use of these sequences in the diagnosis, treatment, and prevention of neurological, endocrine, immunological and cell proliferative disorders.

BACKGROUND OF THE INVENTION

Intercellular communication is essential for the development and survival of multicellular organisms. Cells communicate with one another through the secretion and uptake of protein signaling molecules. The uptake of proteins into the cell is achieved by endocytosis, in which the interaction of signaling molecules with the plasma membrane surface, often via binding to specific receptors, results in the formation of plasma membrane-derived vesicles that enclose and transport the molecules into the cytosol. The secretion of proteins from the cell is achieved by exocytosis, in which molecules inside of the cell are packaged into membrane-bound transport vesicles derived from the trans Golgi network (TGN). These vesicles fuse with the plasma membrane and expel their contents into the surrounding extracellular space. Endocytosis and exocytosis result in the removal and addition of plasma membrane components, and the recycling of these components is essential to maintain the integrity, identity, and functionality of both the plasma membrane and internal membrane-bound compartments.

The endocytic and exocytic pathways converge in internal membrane-bound compartments called endosomes that function in shuttling molecules to and from the TGN and the plasma membrane. In the endocytic pathway, vesicles from the plasma membrane fuse with the endosomal compartment where the internalized signaling molecules dissociate from their receptors. The free receptors are then recycled back to the plasma membrane in vesicles derived from the endosomal compartment. Likewise, in the exocytic pathway, transport vesicles derived from the TGN fuse with the plasma membrane, expel their molecular cargo, and reform. The emptied transport vesicles then recycle back to the TGN via the endosomal compartment.

Certain differentiated cell types have highly specialized and regulated endocytic or exocytic pathways. For example, pancreatic cells package and store digestive enzymes in TGN-derived vesicles called secretion granules until the cells are stimulated by hormonal signals to secrete these enzymes. Similarly, mast cells of the immune system package and store secretion granules containing histamine molecules until stimulated by allergic signals. Neuronal cells package and store neurotransmitters in synaptic vesicles. In response to an action potential, the synaptic vesicles rapidly release their neurotransmitters into the synaptic cleft by fusing with the plasma membrane. The neurotransmitters are taken back up into the neuronal cell by endocytosis, and the neurotransmitters are recycled into synaptic vesicles via the endosomal compartment. (Sudhof, T. C. and Jahn, R. (1991) Neuron 6:665–677; and Sudhof, T. C. et al. (1993) Cell 75:1–4.)

Biochemical and immunocytological studies in rat have shown that TGN- and endosome-derived vesicles contain characteristic integral membrane proteins called SCAMPS, secretory carrier membrane proteins. (Brand, S. H. et al. (1991) J. Biol. Chem. 266:18949–18957.) SCAMP 37, in particular, contains structural motifs that include a potential N-terminal metal ion-binding domain; a leucine zipper domain; two zinc finger nucleotide-binding domains; and four putative membrane-spanning helices. SCAMPs are associated with synaptic vesicles in neuronal cells; secretion granules in endocrine cells; and plasma membrane-derived endocytic vesicles in non-specialized fibroblast cells. (Brand, S. H. and Castle, J. D. (1993) EMBO 12:3753–3761; Laurie, S. M. et al. (1993) J. Biol. Chem. 268:19110–19117.) Because of their ubiquitous presence in vesicles from diverse cellular sources, it is proposed that SCAMPs may play a role in a general cell surface recycling mechanism by regulating vesicular traffic to and from the TGN and plasma membrane. This role would be central to intercellular communication mediated by neurotransmitters, hormones, growth factors, and other signaling molecules involved in cell proliferation and the immune response, and in neurological or endocrine function.

The discovery of new human membrane recycling proteins and the polynucleotides encoding them satisfies a need in the art by providing new compositions which are useful in the diagnosis, treatment, and prevention of neurological, endocrine, immunological and cell proliferative disorders.

SUMMARY OF THE INVENTION

The invention features substantially purified polypeptides, human membrane recycling proteins, referred to collectively as "HMRP" and individually as "HMRP-1" and "HMRP-2." In one aspect, the invention provides a substantially purified polypeptide, HMRP, comprising an amino acid sequence selected from the group consisting of SEQ ID NO:1, SEQ ID NO:3, a fragment of SEQ ID NO:1, and a fragment of SEQ ID NO:3.

The invention further provides a substantially purified variant of HMRP having at least 90% sequence identity to the amino acid sequences of SEQ ID NO:1 or SEQ ID NO:3, or to a fragment of either of these sequences. The invention also provides an isolated and purified polynucleotide encoding the polypeptide comprising an amino acid sequence selected from the group consisting of SEQ ID NO:1, SEQ ID NO:3, a fragment of SEQ ID NO:1, and a fragment of SEQ ID NO:3. The invention also includes an isolated and purified polynucleotide variant having at least 90% sequence identity to the polynucleotide encoding the polypeptide comprising an amino acid sequence selected from the group consisting of SEQ ID NO:1, SEQ ID NO:3, a fragment of SEQ ID NO:1, and a fragment of SEQ ID NO:3.

Additionally, the invention provides a composition comprising a polynucleotide encoding the polypeptide comprising the amino acid sequence selected from the group consisting of SEQ ID NO:1, SEQ ID NO:3, a fragment of SEQ ID NO:1, and a fragment of SEQ ID NO:3. The invention further provides an isolated and purified polynucleotide which hybridizes under stringent conditions to the polynucleotide encoding the polypeptide comprising an amino acid sequence selected from the group consisting of SEQ ID NO:1, SEQ ID NO:3, a fragment of SEQ ID NO:1, and a fragment of SEQ ID NO:3, as well as an isolated and purified polynucleotide which is complementary to the polynucleotide encoding the polypeptide comprising the amino acid sequence selected from the group consisting of SEQ ID NO:1, SEQ ID NO:3, a fragment of SEQ ID NO:1, and a fragment of SEQ ID NO:3.

The invention also provides an isolated and purified polynucleotide comprising a polynucleotide having a sequence selected from the group consisting of SEQ ID NO:2, SEQ ID NO:4, a fragment of SEQ ID NO:2, and a fragment of SEQ ID NO:4. The invention further provides an isolated and purified polynucleotide variant having at least 90% sequence identity to the polynucleotide comprising a polynucleotide having a sequence selected from the group consisting of SEQ ID NO:2, SEQ ID NO:4, a fragment of SEQ ID NO:2, and a fragment of SEQ ID NO:4, as well as an isolated and purified polynucleotide which is complementary to the polynucleotide comprising a polynucleotide having a sequence selected from the group consisting of SEQ ID NO:2, SEQ ID NO:4, a fragment of SEQ ID NO:2, and a fragment of SEQ ID NO:4. The invention also provides a polynucleotide fragment useful for designing oligonucleotides or to be used as a hybridization probe which comprises a polynucleotide having a sequence selected from the group consisting of nucleotides 438–462 of SEQ ID NO:2 and nucleotides 304–330 of SEQ ID NO:4.

The invention further provides an expression vector containing at least a fragment of the polynucleotide encoding the polypeptide comprising an amino acid sequence selected from the group consisting of SEQ ID NO:1, SEQ ID NO:3, a fragment of SEQ ID NO:1, and a fragment of SEQ ID NO:3. In another aspect, the expression vector is contained within a host cell.

The invention also provides a method for producing a polypeptide comprising the amino acid sequence of SEQ ID NO:1, SEQ ID NO:3, a fragment of SEQ ID NO:1, or a fragment of SEQ ID NO:3, the method comprising the steps of: (a) culturing the host cell containing an expression vector containing at least a fragment of a polynucleotide sequence encoding HMRP under conditions suitable for the expression of the polypeptide; and (b) recovering the polypeptide from the host cell culture.

The invention also provides a pharmaceutical composition comprising a substantially purified HMRP having the amino acid sequence of SEQ ID NO:1, SEQ ID NO:3, a fragment of SEQ ID NO:1, or a fragment of SEQ ID NO:3 in conjunction with a suitable pharmaceutical carrier.

The invention further includes a purified antibody which binds to a polypeptide comprising the amino acid sequence of SEQ ID NO:1, SEQ ID NO:3, a fragment of SEQ ID NO:1, or a fragment of SEQ ID NO:3, as well as a purified agonist and a purified antagonist to the polypeptide.

The invention also provides a method for treating or preventing a neurological disorder, the method comprising administering to a subject in need of such treatment an effective amount of a pharmaceutical composition comprising substantially purified HMRP.

The invention also provides a method for treating or preventing an endocrine disorder, the method comprising administering to a subject in need of such treatment an effective amount of a pharmaceutical composition comprising substantially purified HMRP.

The invention also provides a method for treating or preventing an immunological disorder, the method comprising administering to a subject in need of such treatment an effective amount of a pharmaceutical composition comprising substantially purified HMRP.

The invention also provides a method for treating or preventing a cell proliferative disorder, the method comprising administering to a subject in need of such treatment an effective amount of an antagonist of HMRP.

The invention also provides a method for detecting a polynucleotide encoding HMRP in a biological sample containing nucleic acids, the method comprising the steps of: (a) hybridizing the complement of the polynucleotide sequence encoding the polypeptide comprising SEQ ID NO:1, SEQ ID NO:3, a fragment of SEQ ID NO:1, or a fragment of SEQ ID NO:3 to at least one of the nucleic acids of the biological sample, thereby forming a hybridization complex; and (b) detecting the hybridization complex, wherein the presence of the hybridization complex correlates with the presence of a polynucleotide encoding HMRP in the biological sample. In one aspect, the nucleic acids of the biological sample are amplified by the polymerase chain reaction prior to the hybridizing step.

BRIEF DESCRIPTION OF THE FIGURES

FIGS. 1A, 1B, 1C, and 1D show the amino acid sequence (SEQ ID NO:1) and nucleic acid sequence (SEQ ID NO:2) of HMRP-1.

FIGS. 2A, 2B, 2C, 2D, 2E, and 2F show the amino acid sequence (SEQ ID NO:3) and nucleic acid sequence (SEQ ID NO:4) of HMRP-2.

The alignments were produced using MACDNASIS PRO software (Hitachi Software Engineering Co. Ltd., San Bruno, Calif.).

Figure 3A:
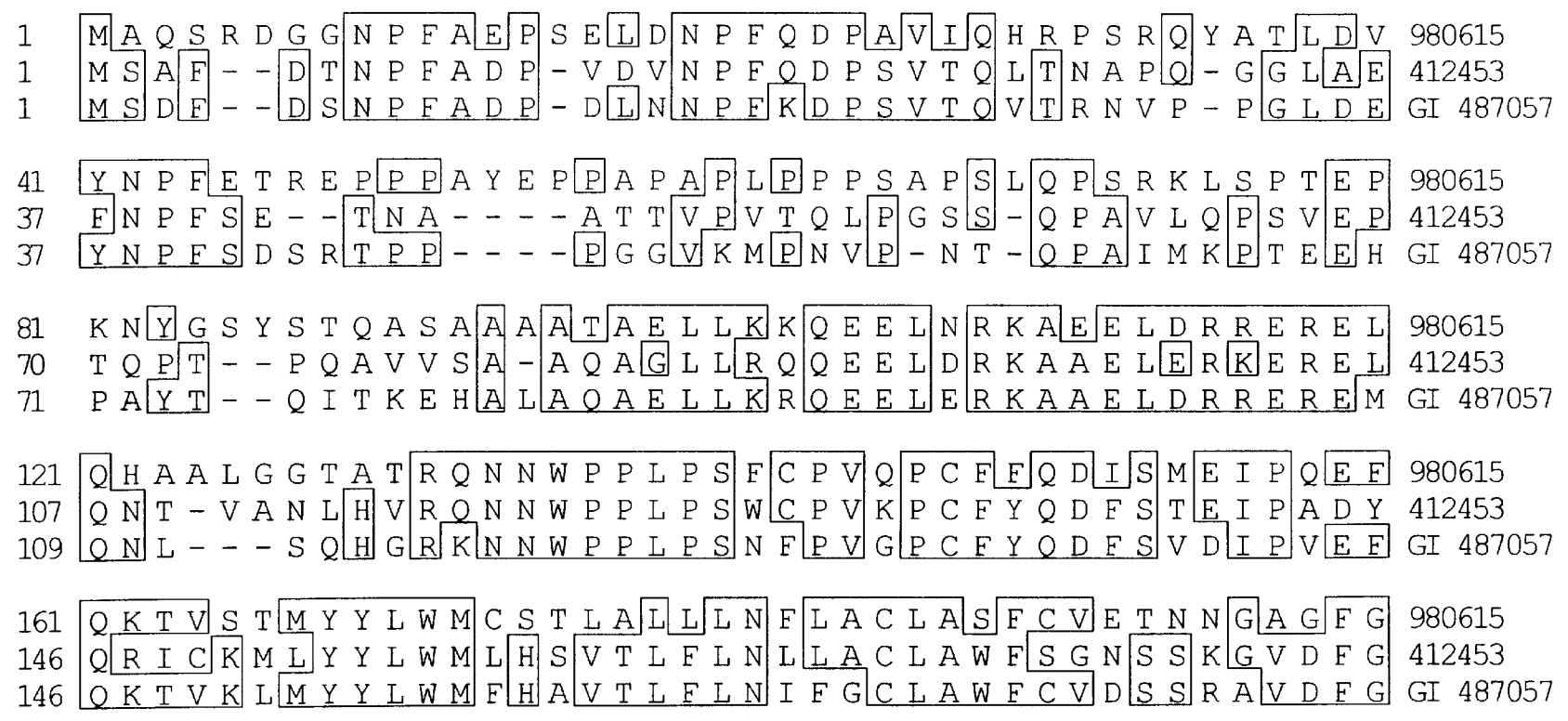
Figure 3B:
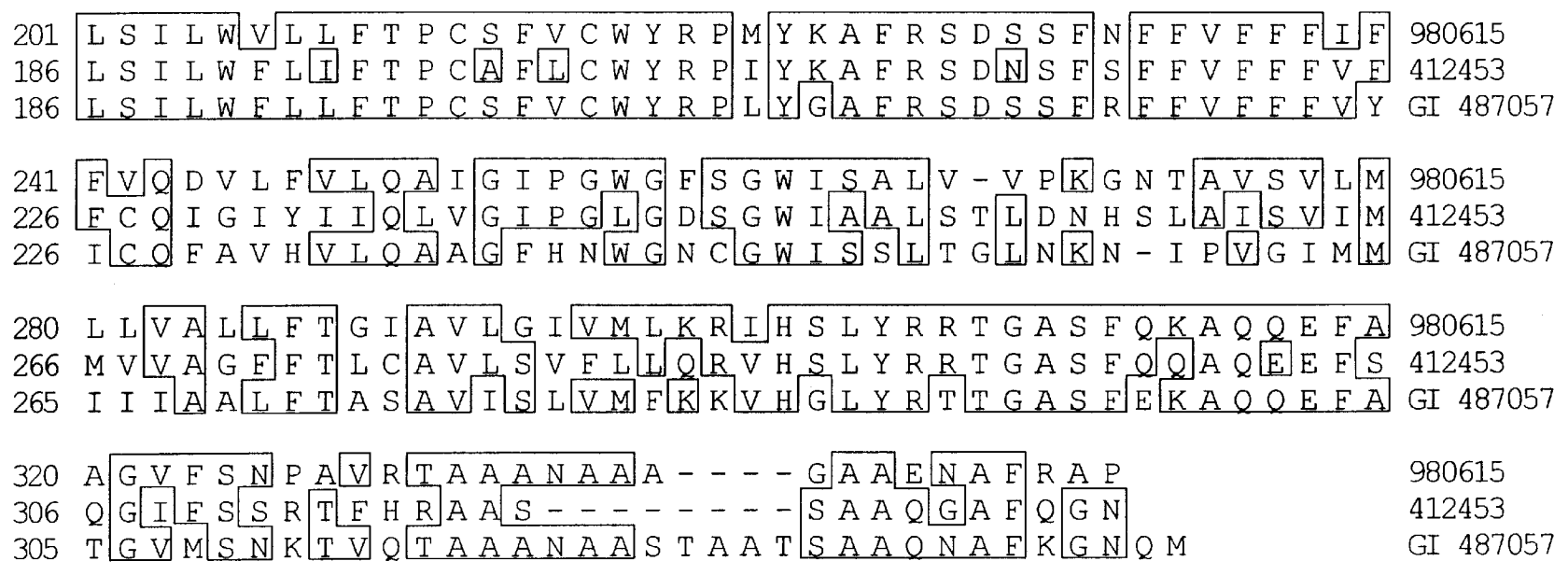

FIGS. 3A and 3B show the amino acid sequence alignments among HMRP-1 (980615; SEQ ID NO:1), HMRP-2 (412453; SEQ ID NO:3), and rat SCAMP 37 (GI 487057; SEQ ID NO:5). The alignments were produced using the multisequence alignment program of DNASTAR software (DNASTAR Inc, Madison Wis.).

DESCRIPTION OF THE INVENTION

Before the present proteins, nucleotide sequences, and methods are described, it is understood that this invention is not limited to the particular methodology, protocols, cell lines, vectors, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "an," and "the" include plural reference unless the context clearly dictates otherwise. Thus, for example, a reference to "a host cell" includes a plurality of such host cells, and a reference to "an antibody" is a reference to one or more antibodies and equivalents thereof known to those skilled in the art, and so forth.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications mentioned herein are cited for the purpose of describing and disclosing the cell lines, vectors, and methodologies which are reported in the publications and which might be used in connection with the invention. Nothing herein is to be construed as an admission that the invention is not entitled to antedate such disclosure by virtue of prior invention.

Definitions

"HMRP," as used herein, refers to the amino acid sequences of substantially purified HMRP obtained from any species, particularly a mammalian species, including bovine, ovine, porcine, murine, equine, and preferably the human species, from any source, whether natural, synthetic, semi-synthetic, or recombinant.

The term "agonist," as used herein, refers to a molecule which, when bound to HMRP, increases or prolongs the duration of the effect of HMRP. Agonists may include proteins, nucleic acids, carbohydrates, or any other molecules which bind to and modulate the effect of HMRP.

An "allele" or an "allelic sequence," as these terms are used herein, is an alternative form of the gene encoding HMRP. Alleles may result from at least one mutation in the nucleic acid sequence and may result in altered mRNAs or in polypeptides whose structure or function may or may not be altered. Any given natural or recombinant gene may have none, one, or many allelic forms. Common mutational changes which give rise to alleles are generally ascribed to natural deletions, additions, or substitutions of nucleotides. Each of these types of changes may occur alone, or in combination with the others, one or more times in a given sequence.

"Altered" nucleic acid sequences encoding HMRP, as described herein, include those sequences with deletions, insertions, or substitutions of different nucleotides, resulting in a polynucleotide the same as HMRP or a polypeptide with at least one functional characteristic of HMRP. Included within this definition are polymorphisms which may or may not be readily detectable using a particular oligonucleotide probe of the polynucleotide encoding HMRP, and improper or unexpected hybridization to alleles, with a locus other than the normal chromosomal locus for the polynucleotide sequence encoding HMRP. The encoded protein may also be "altered," and may contain deletions, insertions, or substitutions of amino acid residues which produce a silent change and result in a functionally equivalent HMRP. Deliberate amino acid substitutions may be made on the basis of similarity in polarity, charge, solubility, hydrophobicity, hydrophilicity, and/or the amphipathic nature of the residues, as long as the biological or immunological activity of HMRP is retained. For example, negatively charged amino acids may include aspartic acid and glutamic acid, positively charged amino acids may include lysine and arginine, and amino acids with uncharged polar head groups having similar hydrophilicity values may include leucine, isoleucine, and valine; glycine and alanine; asparagine and glutamine; serine and threonine; and phenylalanine and tyrosine.

The terms "amino acid" or "amino acid sequence," as used herein, refer to an oligopeptide, peptide, polypeptide, or protein sequence, or a fragment of any of these, and to naturally occurring or synthetic molecules. In this context, "fragments", "immunogenic fragments", or "antigenic fragments" refer to fragments of HMRP which are preferably about 5 to about 15 amino acids in length and which retain some biological activity or immunological activity of HMRP. Where "amino acid sequence" is recited herein to refer to an amino acid sequence of a naturally occurring protein molecule, "amino acid sequence" and like terms are not meant to limit the amino acid sequence to the complete native amino acid sequence associated with the recited protein molecule.

"Amplification," as used herein, relates to the production of additional copies of a nucleic acid sequence. Amplification is generally carried out using polymerase chain reaction (PCR) technologies well known in the art. (See, e.g., Dieffenbach, C. W. and G. S. Dveksler (1995) *PCR Primer, a Laboratory Manual,* Cold Spring Harbor Press, Plainview, N.Y., pp.1–5.)

The term "antagonist," as it is used herein, refers to a molecule which, when bound to HMRP, decreases the amount or the duration of the effect of the biological or immunological activity of HMRP. Antagonists may include proteins, nucleic acids, carbohydrates, antibodies, or any other molecules which decrease the effect of HMRP.

As used herein, the term "antibody" refers to intact molecules as well as to fragments thereof, such as Fab, $F(ab')_2$, and Fv fragments, which are capable of binding the epitopic determinant. Antibodies that bind HMRP polypeptides can be prepared using intact polypeptides or using fragments containing small peptides of interest as the immunizing antigen. The polypeptide or oligopeptide used to immunize an animal (e.g., a mouse, a rat, or a rabbit) can be derived from the translation of RNA, or synthesized chemically, and can be conjugated to a carrier protein if desired. Commonly used carriers that are chemically coupled to peptides include bovine serum albumin, thyroglobulin, and keyhole limpet hemocyanin (KLH). The coupled peptide is then used to immunize the animal.

The term "antigenic determinant," as used herein, refers to that fragment of a molecule (i.e., an epitope) that makes contact with a particular antibody. When a protein or a fragment of a protein is used to immunize a host animal, numerous regions of the protein may induce the production of antibodies which bind specifically to antigenic determinants (given regions or three-dimensional structures on the protein). An antigenic determinant may compete with the intact antigen (i.e., the immunogen used to elicit the immune response) for binding to an antibody.

The term "antisense," as used herein, refers to any composition containing a nucleic acid sequence which is complementary to a specific nucleic acid sequence. The term "antisense strand" is used in reference to a nucleic acid strand that is complementary to the "sense" strand. Antisense molecules may be produced by any method including synthesis or transcription. Once introduced into a cell, the complementary nucleotides combine with natural sequences produced by the cell to form duplexes and to block either transcription or translation. The designation "negative" can refer to the antisense strand, and the designation "positive" can refer to the sense strand.

As used herein, the term "biologically active," refers to a protein having structural, regulatory, or biochemical functions of a naturally occurring molecule. Likewise, "immunologically active" refers to the capability of the natural, recombinant, or synthetic HMRP, or of any oligopeptide thereof, to induce a specific immune response in appropriate animals or cells and to bind with specific antibodies.

The terms "complementary" or "complementarity," as used herein, refer to the natural binding of polynucleotides under permissive salt and temperature conditions by base pairing. For example, the sequence "A-G-T" binds to the complementary sequence "T-C-A." Complementarity between two single-stranded molecules may be "partial," such that only some of the nucleic acids bind, or it may be "complete," such that total complementarity exists between the single stranded molecules. The degree of complementarity between nucleic acid strands has significant effects on the efficiency and strength of the hybridization between the nucleic acid strands. This is of particular importance in amplification reactions, which depend upon binding between nucleic acids strands, and in the design and use of peptide nucleic acid (PNA) molecules.

A "composition comprising a given polynucleotide sequence" or a "composition comprising a given amino acid sequence," as these terms are used herein, refer broadly to any composition containing the given polynucleotide or amino acid sequence. The composition may comprise a dry formulation, an aqueous solution, or a sterile composition. Compositions comprising polynucleotide sequences encoding HMRP or fragments of HMRP may be employed as hybridization probes. The probes may be stored in freeze-dried form and may be associated with a stabilizing agent such as a carbohydrate. In hybridizations, the probe may be deployed in an aqueous solution containing salts (e.g., NaCl), detergents (e.g., SDS), and other components (e.g., Denhardt's solution, dry milk, salmon sperm DNA, etc.).

The phrase "consensus sequence," as used herein, refers to a nucleic acid sequence which has been resequenced to resolve uncalled bases, extended using XL-PCR (Perkin Elmer, Norwalk, Conn.) in the 5' and/or the 3' direction, and resequenced, or which has been assembled from the overlapping sequences of more than one Incyte Clone using a computer program for fragment assembly, such as the GEL-VIEW fragment assembly system (GCG, Madison, Wis.). Some sequences have been both extended and assembled to produce the consensus sequence.

As used herein, the term "correlates with expression of a polynucleotide" indicates that the detection of the presence of nucleic acids, the same or related to a nucleic acid sequence encoding HMRP, by northern analysis is indicative of the presence of nucleic acids encoding HMRP in a sample, and thereby correlates with expression of the transcript from the polynucleotide encoding HMRP.

A "deletion," as the term is used herein, refers to a change in the amino acid or nucleotide sequence that results in the absence of one or more amino acid residues or nucleotides.

The term "derivative," as used herein, refers to the chemical modification of HMRP, of a polynucleotide sequence encoding HMRP, or of a polynucleotide sequence complementary to a polynucleotide sequence encoding HMRP. Chemical modifications of a polynucleotide sequence can include, for example, replacement of hydrogen by an alkyl, acyl, or amino group. A derivative polynucleotide encodes a polypeptide which retains at least one biological or immunological function of the natural molecule. A derivative polypeptide is one modified by glycosylation, pegylation, or any similar process that retains at least one biological or immunological function of the polypeptide from which it was derived.

The term "homology," as used herein, refers to a degree of complementarity. There may be partial homology or complete homology. The word "identity" may substitute for the word "homology." A partially complementary sequence that at least partially inhibits an identical sequence from hybridizing to a target nucleic acid is referred to as "substantially homologous." The inhibition of hybridization of the completely complementary sequence to the target sequence may be examined using a hybridization assay (Southern or northern blot, solution hybridization, and the like) under conditions of reduced stringency. A substantially homologous sequence or hybridization probe will compete for and inhibit the binding of a completely homologous sequence to the target sequence under conditions of reduced stringency. This is not to say that conditions of reduced stringency are such that non-specific binding is permitted, as reduced stringency conditions require that the binding of two sequences to one another be a specific (i.e., a selective) interaction. The absence of non-specific binding may be tested by the use of a second target sequence which lacks even a partial degree of complementarity (e.g., less than about 30% homology or identity). In the absence of non-specific binding, the substantially homologous sequence or probe will not hybridize to the second non-complementary target sequence.

The phrases "percent identity" or "% identity" refer to the percentage of sequence similarity found in a comparison of two or more amino acid or nucleic acid sequences. Percent identity can be determined electronically, e.g., by using the MEGALIGN program (LASERGENE software package, DNASTAR, Inc., Madison Wis.). The MEGALIGN program can create alignments between two or more sequences according to different methods, e.g., the Clustal Method. (Higgins, D. G. and P. M. Sharp (1988) Gene 73:237–244.) The Clustal algorithm groups sequences into clusters by examining the distances between all pairs. The clusters are aligned pairwise and then in groups. The percentage similarity between two amino acid sequences, e.g., sequence A and sequence B, is calculated by dividing the length of sequence A, minus the number of gap residues in sequence A, minus the number of gap residues in sequence B, into the sum of the residue matches between sequence A and sequence B, times one hundred. Gaps of low or of no homology between the two amino acid sequences are not included in determining percentage similarity. Percent identity between nucleic acid sequences can also be calculated by the Clustal Method, or by other methods known in the art, such as the Jotun Hein Method. (See, e.g., Hein, J. (1990) Methods in Enzymology 183:626–645.) Identity between sequences can also be determined by other methods known in the art, e.g., by varying hybridization conditions.

"Human artificial chromosomes" (HACs), as described herein, are linear microchromosomes which may contain DNA sequences of about 6 kb to 10 Mb in size, and which contain all of the elements required for stable mitotic chromosome segregation and maintenance. (See, e.g., Harrington, J. J. et al. (1997) Nat Genet. 15:345–355.)

The term "humanized antibody," as used herein, refers to antibody molecules in which the amino acid sequence in the non-antigen binding regions has been altered so that the antibody more closely resembles a human antibody, and still retains its original binding ability.

"Hybridization," as the term is used herein, refers to any process by which a strand of nucleic acid binds with a complementary strand through base pairing.

As used herein, the term "hybridization complex", refers to a complex formed between two nucleic acid sequences by virtue of the formation of hydrogen bonds between complementary bases. A hybridization complex may be formed in solution (e.g., $C_0t$ or $R_0t$ analysis) or formed between one nucleic acid sequence present in solution and another nucleic acid sequence immobilized on a solid support (e.g., paper, membranes, filters, chips, pins or glass slides, or any other appropriate substrate to which cells or their nucleic acids have been fixed).

"Immune response" can refer to conditions associated with inflammation, trauma, immune disorders, or infectious or genetic disease, etc. These conditions can be characterized by expression of various factors, e.g., cytokines, chemokines, and other signaling molecules, which may affect cellular and systemic defense systems.

The words "insertion" or "addition," as used herein, refer to changes in an amino acid or nucleotide sequence resulting in the addition of one or more amino acid residues or nucleotides, respectively, to the sequence found in the naturally occurring molecule.

The term "microarray," as used herein, refers to an array of distinct polynucleotides or oligonucleotides arrayed on a substrate, such as paper, nylon or any other type of membrane, filter, chip, glass slide, or any other suitable solid support.

The term "modulate," as it appears herein, refers to a change in the activity of HMRP. For example, modulation may cause an increase or a decrease in protein activity, binding characteristics, or any other biological, functional, or immunological properties of HMRP.

The phrases "nucleic acid" or "nucleic acid sequence," as used herein, refer to an oligonucleotide, nucleotide, polynucleotide, or any fragment thereof, to DNA or RNA of genomic or synthetic origin which may be single-stranded or double-stranded and may represent the sense or the antisense strand, to peptide nucleic acid (PNA), or to any DNA-like or RNA-like material. In this context, "fragments" refers to those nucleic acid sequences which are greater than about 60 nucleotides in length, and most preferably are at least about 100 nucleotides, at least about 1000 nucleotides, or at least about 10,000 nucleotides in length.

The term "oligonucleotide," as used herein, refers to a nucleic acid sequence of at least about 6 nucleotides to 60 nucleotides, preferably about 15 to 30 nucleotides, and most preferably about 20 to 25 nucleotides, which can be used in PCR amplification or in a hybridization assay or microarray. As used herein, the term "oligonucleotide" is substantially equivalent to the terms "amplimers," "primers," "oligomers," and "probes," as these terms are commonly defined in the art.

"Peptide nucleic acid" (PNA), as used herein, refers to an antisense molecule or anti-gene agent which comprises an oligonucleotide of at least about 5 nucleotides in length linked to a peptide backbone of amino acid residues ending in lysine. The terminal lysine confers solubility to the composition. PNAs preferentially bind complementary single stranded DNA and RNA and stop transcript elongation, and may be pegylated to extend their lifespan in the cell. (See, e.g., Nielsen, P. E. et al. (1993) Anticancer Drug Des. 8:53–63.)

The term "sample," as used herein, is used in its broadest sense. A biological sample suspected of containing nucleic acids encoding HMRP, or fragments thereof, or HMRP itself may comprise a bodily fluid; an extract from a cell, chromosome, organelle, or membrane isolated from a cell; a cell; genomic DNA, RNA, or cDNA (in solution or bound to a solid support); a tissue; a tissue print; and the like.

As used herein, the terms "specific binding" or "specifically binding" refer to that interaction between a protein or peptide and an agonist, an antibody, or an antagonist. The interaction is dependent upon the presence of a particular structure of the protein recognized by the binding molecule (i.e., the antigenic determinant or epitope). For example, if an antibody is specific for epitope "A," the presence of a polypeptide containing the epitope A, or the presence of free unlabeled A, in a reaction containing free labeled A and the antibody will reduce the amount of labeled A that binds to the antibody.

As used herein, the term "stringent conditions" refers to conditions which permit hybridization between polynucleotide sequences and the claimed polynucleotide sequences. Suitably stringent conditions can be defined by, for example, the concentrations of salt or formamide in the prehybridization and hybridization solutions, or by the hybridization temperature, and are well known in the art. In particular, stringency can be increased by reducing the concentration of salt, increasing the concentration of formamide, or raising the hybridization temperature.

For example, hybridization under high stringency conditions could occur in about 50% formamide at about 37° C. to 42° C. Hybridization could occur under reduced stringency conditions in about 35% to 25% formamide at about 30° C. to 35° C. In particular, hybridization could occur under high stringency conditions at 42° C. in 50% formamide, 5×SSPE, 0.3% SDS, and 200 µg/ml sheared and denatured salmon sperm DNA. Hybridization could occur under reduced stringency conditions as described above, but in 35% formamide at a reduced temperature of 35° C. The temperature range corresponding to a particular level of stringency can be further narrowed by calculating the purine to pyrimidine ratio of the nucleic acid of interest and adjusting the temperature accordingly. Variations on the above ranges and conditions are well known in the art.

The term "substantially purified," as used herein, refers to nucleic acid or amino acid sequences that are removed from their natural environment and are isolated or separated, and are at least about 60% free, preferably about 75% free, and most preferably about 90% free from other components with which they are naturally associated.

A "substitution," as used herein, refers to the replacement of one or more amino acids or nucleotides by different amino acids or nucleotides, respectively.

"Transformation," as defined herein, describes a process by which exogenous DNA enters and changes a recipient cell. Transformation may occur under natural or artificial conditions according to various methods well known in the art, and may rely on any known method for the insertion of foreign nucleic acid sequences into a prokaryotic or eukaryotic host cell. The method for transformation is selected based on the type of host cell being transformed and may include, but is not limited to, viral infection, electroporation, heat shock, lipofection, and particle bombardment. The term "transformed" cells includes stably transformed cells in which the inserted DNA is capable of replication either as an autonomously replicating plasmid or as part of the host chromosome, and refers to cells which transiently express the inserted DNA or RNA for limited periods of time.

A "variant" of HMRP, as used herein, refers to an amino acid sequence that is altered by one or more amino acids. The variant may have "conservative" changes, wherein a substituted amino acid has similar structural or chemical properties (e.g., replacement of leucine with isoleucine). More rarely, a variant may have "nonconservative" changes (e.g., replacement of glycine with tryptophan). Analogous minor variations may also include amino acid deletions or insertions, or both. Guidance in determining which amino acid residues may be substituted, inserted, or deleted without abolishing biological or immunological activity may be found using computer programs well known in the art, for example, DNASTAR software.

The Invention

The invention is based on the discovery of new human membrane recycling proteins (HMRP), the polynucleotides encoding HMRP, and the use of these compositions for the diagnosis, treatment, or prevention of neurological, endocrine, immunological and cell proliferative disorders.

Nucleic acids encoding the HMRP-1 of the present invention were first identified in Incyte Clone 980615 from the tongue tumor cDNA library (TONGTUT01) using a computer search for amino acid sequence alignments. A consensus sequence, SEQ ID NO:2, was derived from the following overlapping and/or extended nucleic acid sequences: Incyte Clones 3841666 (DENDNOT01), 1513267 (PANCTUT01), 154957 (THPIPLB02), 1628138 (COLNPOT01), 980615 (TONGTUT01), 364646 (PROSNOT01), and 1923134 (BRSTTUT01).

In one embodiment, the invention encompasses a polypeptide comprising the amino acid sequence of SEQ ID NO:1, as shown in FIGS. 1A, 1B, 1C, and 1D. HMRP-1 is 347 amino acids in length and has a potential cAMP- and cGMP-dependent protein kinase phosphorylation site at residue $S_{76}$; two potential casein kinase II phosphorylation sites at $S_{15}$ and $S_{76}$; a potential protein kinase C phosphorylation site at $S_{72}$; and a leucine zipper pattern comprising amino acids $L_{99}$ through $L_{120}$. As shown in FIGS. 3A and 3B, HMRP-1 has chemical and structural homology with rat SCAMP 37 (GI 487057; SEQ ID NO:5). In particular, HMRP-1 shares 49% identity with rat SCAMP 37. The leucine zipper pattern of HMRP-1 shares 82% identity with that of rat SCAMP 37. The region of HMRP-1 from $C_{185}$ to $C_{216}$ shares 72% identity with one of the putative zinc-finger nucleotide-binding domains of rat SCAMP 37 and shows conservation of all four potential zinc-coordinating cysteines at $C_{185}$, $C_{190}$, $C_{212}$, and $C_{216}$. In addition, hydrophobic residues within the four putative transmembrane domains (TM) are conserved between the two proteins. Within HMRP-1, TM1 extends from about $T_{166}$ to about $V_{191}$; TM2, from about $F_{199}$ to about $W_{217}$; TM3, from about $F_{233}$ to about $I_{254}$; and TM4, from about $T_{273}$ to about $L_{297}$. A fragment of the HMRP-1 nucleic acid sequence useful for designing oligonucleotides or to be used directly as a hybridization probe to distinguish between the sequences encoding HMRP-1 and rat SCAMP 37 comprises nucleotides 438–462. Northern analysis shows the expression of HMRP-1 in various libraries, at least 64% of which involve cell proliferation and at least 27% of which involve immune response. Of particular note is the expression of HMRP-1 in reproductive, neuronal, gastrointestinal, and hematopoietic tissues that actively employ transport vesicle-mediated secretion mechanisms.

Nucleic acids encoding the HMRP-2 of the present invention were first identified in Incyte Clone 412453 from the breast tissue cDNA library (BRSTNOT01) using a computer search for amino acid sequence alignments. A consensus sequence, SEQ ID NO:4, was derived from the following overlapping and/or extended nucleic acid sequences: Incyte Clones 1256847 (MENITUT03), 639585 (BRSTNOT03), 1333295 (COLNNOT13), 1435380 (PANCNOT08), 412453 (BRSTNOT01), 2873157 (THYRNOT10), 776678 (COLNNOT05), 834309 (PROSNOT07), 815923 (OVARTUT01), and 1240683 (LUNGNOT03).

In another embodiment, the invention encompasses a polypeptide comprising the amino acid sequence of SEQ ID NO:3, as shown in FIGS. 2A, 2B, 2C, 2D, 2E, and 2F. HMRP-2 is 329 amino acids in length and has two potential N-glycosylation sites at $N_{177}$ and $N_{256}$; two potential casein kinase II phosphorylation sites at $S_2$ and $S_{252}$; two potential protein kinase C phosphorylation sites at $S_{178}$ and $S_{310}$; and two leucine zipper patterns comprising amino acids $L_{85}$ through $L_{106}$ and $L_{92}$ through $L_{113}$. As shown in FIGS. 3A and 3B, HMRP-2 has chemical and structural homology with rat SCAMP 37 (GI 487057; SEQ ID NO:5). In particular, HMRP-2 shares 50% identity with rat SCAMP 37. The leucine zipper pattern of HMRP-2 shares 73% identity with that of rat SCAMP 37. The region of HMRP-2 from $C_{170}$ to $C_{201}$, shares 75% identity with one of the putative zinc-finger nucleotide-binding domains of rat SCAMP 37 and shows conservation of three of the four potential zinc-coordinating cysteines at $C_{170}$, $C_{197}$, and $C_{201}$. Residues $D_5$, $N_7$, $F_9$, and $D_{11}$ of HMRP-2 are identical to four of six putative metal ion-coordinating residues in the equivalent positions of the rat SCAMP 37 N-terminus. The potential phosphorylation sites at $S_2$, S178, and $S_{310}$ are conserved between the two proteins. In addition, hydrophobic residues within the four putative transmembrane domains (TM) are conserved. Within HMRP-2, TM1 extends from about $M_{151}$ to about $G_{176}$; TM2, from about $F_{184}$ to about $W_{202}$; TM3, from about $F_{218}$ to about $I_{239}$; and TM4, from about $L_{259}$ to about $L_{283}$. A fragment of the HMRP-2 nucleic acid sequence useful for designing oligonucleotides or to be used directly as a hybridization probe to distinguish between the sequences encoding HMRP-2 and rat SCAMP 37 comprises nucleotides 304–330. Northern analysis shows the expression of HMRP-2 in various libraries, at least 66% of which involve cell proliferation and at least 32% of which involve immune response. Of particular note is the expression of HMRP-2 in reproductive, gastrointestinal, hematopoietic, and neuronal tissues that actively employ transport vesicle-mediated secretion mechanisms.

The invention also encompasses HMRP variants. A preferred HMRP variant is one which has at least about 80%, more preferably at least about 90%, and most preferably at least about 95% amino acid sequence identity to the HMRP amino acid sequence, and which contains at least one functional or structural characteristic of HMRP.

The invention also encompasses polynucleotides which encode HMRP. In a particular embodiment, the invention encompasses a polynucleotide sequence comprising the sequence of SEQ ID NO:2, which encodes an HMRP-1, as shown in FIGS. 1A, 1B, 1C, and 1D. In a further embodiment, the invention encompasses a polynucleotide sequence comprising the sequence of SEQ ID NO:4, which encodes an HMRP-2, as shown in FIGS. 2A, 2B, 2C, 2D, 2E, and 2F.

The invention also encompasses a variant of a polynucleotide sequence encoding HMRP. In particular, such a variant polynucleotide sequence will have at least about 80%, more preferably at least about 90%, and most preferably at least about 95% polynucleotide sequence identity to the polynucleotide sequence encoding HMRP. A particular aspect of the invention encompasses a variant of SEQ ID NO:2 which has at least about 80%, more preferably at least about 90%, and most preferably at least about 95% polynucleotide sequence identity to SEQ ID NO:2. The invention further encompasses a polynucleotide variant of SEQ ID NO:4 having at least about 80%, more preferably at least about 90%, and most preferably at least about 95% polynucleotide sequence identity to SEQ ID NO:4. Any one of the polynucleotide variants described above can encode an amino acid sequence which contains at least one functional or structural characteristic of HMRP.

It will be appreciated by those skilled in the art that as a result of the degeneracy of the genetic code, a multitude of polynucleotide sequences encoding HMRP, some bearing minimal homology to the polynucleotide sequences of any known and naturally occurring gene, may be produced. Thus, the invention contemplates each and every possible variation of polynucleotide sequence that could be made by selecting combinations based on possible codon choices. These combinations are made in accordance with the standard triplet genetic code as applied to the polynucleotide sequence of naturally occurring HMRP, and all such variations are to be considered as being specifically disclosed.

Although nucleotide sequences which encode HMRP and its variants are preferably capable of hybridizing to the nucleotide sequence of the naturally occurring HMRP under appropriately selected conditions of stringency, it may be advantageous to produce nucleotide sequences encoding HMRP or its derivatives possessing a substantially different codon usage. Codons may be selected to increase the rate at which expression of the peptide occurs in a particular prokaryotic or eukaryotic host in accordance with the frequency with which particular codons are utilized by the host. Other reasons for substantially altering the nucleotide sequence encoding HMRP and its derivatives without altering the encoded amino acid sequences include the production of RNA transcripts having more desirable properties, such as a greater half-life, than transcripts produced from the naturally occurring sequence.

The invention also encompasses production of DNA sequences which encode HMRP and HMRP derivatives, or fragments thereof, entirely by synthetic chemistry. After production, the synthetic sequence may be inserted into any of the many available expression vectors and cell systems using reagents that are well known in the art. Moreover, synthetic chemistry may be used to introduce mutations into a sequence encoding HMRP or any fragment thereof.

Also encompassed by the invention are polynucleotide sequences that are capable of hybridizing to the claimed polynucleotide sequences, and, in particular, to those shown in SEQ ID NO:2, SEQ ID NO:4, a fragment of SEQ ID NO:2, or a fragment of SEQ ID NO:4, under various conditions of stringency. (See, e.g., Wahl, G. M. and S. L. Berger (1987) Methods Enzymol. 152:399–407; and Kimmel, A. R. (1987) Methods Enzymol. 152:507–511.)

Methods for DNA sequencing are well known and generally available in the art and may be used to practice any of the embodiments of the invention. The methods may employ such enzymes as the Klenow fragment of DNA polymerase I, SEQUENASE (US Biochemical Corp., Cleveland, Ohio), Taq polymerase (Perkin Elmer), thermostable T7 polymerase (Amersham, Chicago, Ill.), or combinations of polymerases and proofreading exonucleases such as those found in the ELONGASE amplification system (GIBCO/BRL Gaithersburg, Md.). Preferably, the process is automated with machines such as the MICROLAB 2200 (Hamilton, Reno, Nev.), Peltier thermal cycler (PTC200; MJ Research, Watertown, Mass.), and the ABI Catalyst and 373 and 377 DNA sequencers (Perkin Elmer).

The nucleic acid sequences encoding HMRP may be extended utilizing a partial nucleotide sequence and employing various methods known in the art to detect upstream sequences, such as promoters and regulatory elements. For example, one method which may be employed, restriction-site PCR, uses universal primers to retrieve unknown sequence adjacent to a known locus. (See, e.g., Sarkar, G. (1993) PCR Methods Applic. 2:318–322.) In particular, genomic DNA is first amplified in the presence of a primer to a linker sequence and a primer specific to the known region. The amplified sequences are then subjected to a second round of PCR with the same linker primer and another specific primer internal to the first one. Products of each round of PCR are transcribed with an appropriate RNA polymerase and sequenced using reverse transcriptase.

Inverse PCR may also be used to amplify or extend sequences using divergent primers based on a known region. (See, e.g., Triglia, T. et al. (1988) Nucleic Acids Res. 16:8186.) The primers may be designed using commercially available software such as OLIGO 4.06 primer analysis software (National Biosciences Inc., Plymouth, Minn.) or another appropriate program to be about 22 to 30 nucleotides in length, to have a GC content of about 50% or more, and to anneal to the target sequence at temperatures of about 68° C. to 72° C. The method uses several restriction enzymes to generate a suitable fragment in the known region of a gene. The fragment is then circularized by intramolecular ligation and used as a PCR template.

Another method which may be used is capture PCR, which involves PCR amplification of DNA fragments adjacent to a known sequence in human and yeast artificial chromosome DNA. (See, e.g., Lagerstrom, M. et al. (1991) PCR Methods Applic. 1:111–119.) In this method, multiple restriction enzyme digestions and ligations may be used to place an engineered double-stranded sequence into an unknown fragment of the DNA molecule before performing PCR. Other methods which may be used to retrieve unknown sequences are known in the art. (See, e.g., Parker, J. D. et al. (1991) Nucleic Acids Res. 19:3055–3060.) Additionally, one may use PCR, nested primers, PROMOTERFINDER libraries to walk genomic DNA (Clontech, Palo Alto, Calif.). This process avoids the need to screen libraries and is useful in finding intron/exon junctions.

When screening for full-length cDNAs, it is preferable to use libraries that have been size-selected to include larger cDNAs. Also, random-primed libraries are preferable in that they will include more sequences which contain the 5' regions of genes. Use of a randomly primed library may be especially preferable for situations in which an oligo d(T) library does not yield a full-length cDNA. Genomic libraries may be useful for extension of sequence into 5' non-transcribed regulatory regions.

Capillary electrophoresis systems which are commercially available may be used to analyze the size or confirm the nucleotide sequence of sequencing or PCR products. In particular, capillary sequencing may employ flowable polymers for electrophoretic separation, four different fluorescent dyes (one for each nucleotide) which are laser activated, and a charge coupled device camera for detection of the emitted wavelengths. Output/light intensity may be converted to electrical signal using appropriate software (e.g., GENOTYPER and SEQUENCE NAVIGATOR, Perkin Elmer), and the entire process from loading of samples to computer analysis and electronic data display may be computer controlled. Capillary electrophoresis is especially preferable for the sequencing of small pieces of DNA which might be present in limited amounts in a particular sample.

In another embodiment of the invention, polynucleotide sequences or fragments thereof which encode HMRP may be used in recombinant DNA molecules to direct expression of HMRP, or fragments or functional equivalents thereof, in appropriate host cells. Due to the inherent degeneracy of the genetic code, other DNA sequences which encode substantially the same or a functionally equivalent amino acid sequence may be produced, and these sequences may be used to clone and express HMRP.

As will be understood by those of skill in the art, it may be advantageous to produce HMRP-encoding nucleotide sequences possessing non-naturally occurring codons. For example, codons preferred by a particular prokaryotic or eukaryotic host can be selected to increase the rate of protein expression or to produce an RNA transcript having desirable properties, such as a half-life which is longer than that of a transcript generated from the naturally occurring sequence.

The nucleotide sequences of the present invention can be engineered using methods generally known in the art in order to alter HMRP encoding sequences for a variety of reasons including, but not limited to, alterations which modify the cloning, processing, and/or expression of the gene product. DNA shuffling by random fragmentation and PCR reassembly of gene fragments and synthetic oligonucleotides may be used to engineer the nucleotide sequences. For example, site-directed mutagenesis may be used to insert new restriction sites, alter glycosylation patterns, change codon preference, produce splice variants, introduce mutations, and so forth.

In another embodiment of the invention, natural, modified, or recombinant nucleic acid sequences encoding HMRP may be ligated to a heterologous sequence to encode a fusion protein. For example, to screen peptide libraries for inhibitors of HMRP activity, it may be useful to encode a chimeric HMRP protein that can be recognized by a commercially available antibody. A fusion protein may also be engineered to contain a cleavage site located between the HMRP encoding sequence and the heterologous protein sequence, so that HMRP may be cleaved and purified away from the heterologous moiety.

In another embodiment, sequences encoding HMRP may be synthesized, in whole or in part, using chemical methods well known in the art. (See, e.g., Caruthers, M. H. et al. (1980) Nucl. Acids Res. Symp. Ser. 215–223; and Horn, T. et al. (1980) Nucl. Acids Res. Symp. Ser. 225–232.) Alternatively, the protein itself may be produced using chemical methods to synthesize the amino acid sequence of HMRP, or a fragment thereof. For example, peptide synthesis can be performed using various solid-phase techniques. (Roberge, J. Y. et al. (1995) Science 269:202–204.) Automated synthesis may be achieved using the ABI 431 A peptide synthesizer (Perkin Elmer).

The newly synthesized peptide may be substantially purified by preparative high performance liquid chromatography. (See, e.g, Chiez, R. M. and F. Z. Regnier (1990) Methods Enzymol. 182:392–421.) The composition of the synthetic peptides may be confirmed by amino acid analysis or by sequencing. (See, e.g., Creighton, T. (1983) *Proteins, Structures and Molecular Properties,* WH Freeman and Co., New York, N.Y.) Additionally, the amino acid sequence of HMRP, or any part thereof, may be altered during direct synthesis and/or combined with sequences from other proteins, or any part thereof, to produce a variant polypeptide.

In order to express a biologically active HMRP, the nucleotide sequences encoding HMRP or derivatives thereof may be inserted into an appropriate expression vector, i.e., a vector which contains the necessary elements for the transcription and translation of the inserted coding sequence.

Methods which are well known to those skilled in the art may be used to construct expression vectors containing sequences encoding HMRP and appropriate transcriptional and translational control elements. These methods include in vitro recombinant DNA techniques, synthetic techniques, and in vivo genetic recombination. (See, e.g., Sambrook, J. et al. (1989) *Molecular Cloning, A Laboratory Manual,* Cold Spring Harbor Press, Plainview, N.Y., ch. 4, 8, and 16–17; and Ausubel, F. M. et al. (1995, and periodic supplements) *Current Protocols in Molecular Biology,* John Wiley & Sons, New York, N.Y., ch. 9, 13, and 16.)

A variety of expression vector/host systems may be utilized to contain and express sequences encoding HMRP. These include, but are not limited to, microorganisms such as bacteria transformed with recombinant bacteriophage, plasmid, or cosmid DNA expression vectors; yeast transformed with yeast expression vectors; insect cell systems infected with virus expression vectors (e.g., baculovirus); plant cell systems transformed with virus expression vectors (e.g., cauliflower mosaic virus (CaMV) or tobacco mosaic virus (TMV)) or with bacterial expression vectors (e.g., Ti or pBR322 plasmids); or animal cell systems. The invention is not limited by the host cell employed.

The "control elements" or "regulatory sequences" are those non-translated regions of the vector (i.e., enhancers, promoters, and 5' and 3' untranslated regions) which interact with host cellular proteins to carry out transcription and translation. Such elements may vary in their strength and specificity. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT phagemid (Stratagene, La Jolla, Calif.) or PSPORT1 plasmid (GIBCO/BRL), and the like, may be used. The baculovirus polyhedrin promoter may be used in insect cells. Promoters or enhancers derived from the genomes of plant cells (e.g., heat shock, RUBISCO, and storage protein genes) or from plant viruses (e.g., viral promoters or leader sequences) may be cloned into the vector. In mammalian cell systems, promoters from mammalian genes or from mammalian viruses are preferable. If it is necessary to generate a cell line that contains multiple copies of the sequence encoding HMRP, vectors based on SV40 or EBV may be used with an appropriate selectable marker.

In bacterial systems, a number of expression vectors may be selected depending upon the use intended for HMRP. For example, when large quantities of HMRP are needed for the induction of antibodies, vectors which direct high level expression of fusion proteins that are readily purified may be used. Such vectors include, but are not limited to, multifunctional *E. coli* cloning and expression vectors such as BLUESCRIPT (Stratagene), in which the sequence encoding HMRP may be ligated into the vector in frame with sequences for the amino-terminal Met and the subsequent 7 residues of β-galactosidase so that a hybrid protein is produced; pIN vectors (See, e.g., Van Heeke, G. and S. M. Schuster (1989) J. Biol. Chem. 264:5503–5509.); pGEX vectors (Promega, Madison, Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems may be designed to include heparin, thrombin, or factor XA protease cleavage sites so that the cloned polypeptide of interest can be released from the GST moiety at will.

In the yeast *Saccharomyces cerevisiae,* a number of vectors containing constitutive or inducible promoters, such as alpha factor, alcohol oxidase, and PGH, may be used. (See, e.g., Ausubel, supra; and Grant et al. (1987) Methods Enzymol. 153:516–544.)

In cases where plant expression vectors are used, the expression of sequences encoding HMRP may be driven by any of a number of promoters. For example, viral promoters such as the 35S and 19S promoters of CaMV may be used alone or in combination with the omega leader sequence from TMV. (Takamatsu, N. (1987) EMBO J. 6:307–311.) Alternatively, plant promoters such as the small subunit of RUBISCO or heat shock promoters may be used. (See, e.g., Coruzzi, G. et al. (1984) EMBO J. 3:1671–1680; Broglie, R. et al. (1984) Science 224:838–843; and Winter, J. et al. (1991) Results Probl. Cell Differ. 17:85–105.) These constructs can be introduced into plant cells by direct DNA transformation or pathogen-mediated transfection. Such techniques are described in a number of generally available reviews. (See, e.g., Hobbs, S. or Murry, L. E. in *McGraw Hill Yearbook of Science and Technology* (1992) McGraw Hill, New York, N.Y.; pp. 191–196.)

An insect system may also be used to express HMRP. For example, in one such system, Autographa californica nuclear polyhedrosis virus (AcNPV) is used as a vector to express foreign genes in *Spodoptera frugiperda* cells or in Trichoplusia larvae. The sequences encoding HMRP may be cloned into a non-essential region of the virus, such as the polyhedrin gene, and placed under control of the polyhedrin promoter. Successful insertion of HMRP will render the polyhedrin gene inactive and produce recombinant virus lacking coat protein. The recombinant viruses may then be used to infect, for example, *S. frugiperda* cells or Trichoplusia larvae in which HMRP may be expressed. (See, e.g., Engelhard, E. K. et al. (1994) Proc. Nat. Acad. Sci. 91:3224–3227.)

In mammalian host cells, a number of viral-based expression systems may be utilized. In cases where an adenovirus is used as an expression vector, sequences encoding HMRP may be ligated into an adenovirus transcription/translation complex consisting of the late promoter and tripartite leader sequence. Insertion in a non-essential E1 or E3 region of the viral genome may be used to obtain a viable virus which is capable of expressing HMRP in infected host cells. (See, e.g., Logan, J. and T. Shenk (1984) Proc. Natl. Acad. Sci. 81:3655–3659.) In addition, transcription enhancers, such as the Rous sarcoma virus (RSV) enhancer, may be used to increase expression in mammalian host cells.

Human artificial chromosomes (HACs) may also be employed to deliver larger fragments of DNA than can be contained and expressed in a plasmid. HACs of about 6 kb to 10 Mb are constructed and delivered via conventional delivery methods (liposomes, polycationic amino polymers, or vesicles) for therapeutic purposes.

Specific initiation signals may also be used to achieve more efficient translation of sequences encoding HMRP. Such signals include the ATG initiation codon and adjacent sequences. In cases where sequences encoding HMRP and its initiation codon and upstream sequences are inserted into the appropriate expression vector, no additional transcriptional or translational control signals may be needed. However, in cases where only coding sequence, or a fragment thereof, is inserted, exogenous translational control signals including the ATG initiation codon should be provided. Furthermore, the initiation codon should be in the correct reading frame to ensure translation of the entire insert. Exogenous translational elements and initiation codons may be of various origins, both natural and synthetic. The efficiency of expression may be enhanced by the inclusion of enhancers appropriate for the particular cell system used. (See, e.g., Scharf, D. et al. (1994) Results Probl. Cell Differ. 20:125–162.)

In addition, a host cell strain may be chosen for its ability to modulate expression of the inserted sequences or to process the expressed protein in the desired fashion. Such modifications of the polypeptide include, but are not limited to, acetylation, carboxylation, glycosylation, phosphorylation, lipidation, and acylation. Post-translational processing which cleaves a "prepro" form of the protein may also be used to facilitate correct insertion, folding, and/or function. Different host cells which have specific cellular machinery and characteristic mechanisms for post-translational activities (e.g., CHO, HeLa, MDCK, HEK293, and WI38), are available from the American Type Culture Collection (ATCC, Bethesda, Md.) and may be chosen to ensure the correct modification and processing of the foreign protein.

For long term, high yield production of recombinant proteins, stable expression is preferred. For example, cell lines capable of stably expressing HMRP can be transformed using expression vectors which may contain viral origins of replication and/or endogenous expression elements and a selectable marker gene on the same or on a separate vector. Following the introduction of the vector, cells may be allowed to grow for about 1 to 2 days in enriched media before being switched to selective media. The purpose of the selectable marker is to confer resistance to selection, and its presence allows growth and recovery of cells which successfully express the introduced sequences. Resistant clones of stably transformed cells may be proliferated using tissue culture techniques appropriate to the cell type.

Any number of selection systems may be used to recover transformed cell lines. These include, but are not limited to, the herpes simplex virus thymidine kinase genes and adenine phosphoribosyltransferase genes, which can be employed in tk$^-$ or apr$^-$ cells, respectively. (See, e.g., Wigler, M. et al. (1977) Cell 11:223–232; and Lowy, I. et al. (1980) Cell 22:817–823) Also, antimetabolite, antibiotic, or herbicide resistance can be used as the basis for selection. For example, dhfr confers resistance to methotrexate; npt confers resistance to the aminoglycosides neomycin and G-418; and als or pat confer resistance to chlorsulfuron and phosphinotricin acetyltransferase, respectively. (See, e.g., Wigler, M. et al. (1980) Proc. Natl. Acad. Sci. 77:3567–3570; Colbere-Garapin, F. et al (1981) J. Mol. Biol. 150:1–14; and Murry, supra.) Additional selectable genes have been described, e.g., trpB, which allows cells to utilize indole in place of tryptophan, or hisD, which allows cells to utilize histinol in place of histidine. (See, e.g., Hartman, S. C. and R. C. Mulligan (1988) Proc. Natl. Acad. Sci. 85:8047–8051.) Recently, the use of visible markers has gained popularity with such markers as anthocyanins, β glucuronidase and its substrate GUS, and luciferase and its substrate luciferin. These markers can be used not only to identify transformants, but also to quantify the amount of transient or stable protein expression attributable to a specific vector system. (See, e.g., Rhodes, C. A. et al. (1995) Methods Mol. Biol. 55:121–131.)

Although the presence/absence of marker gene expression suggests that the gene of interest is also present, the presence and expression of the gene may need to be confirmed. For example, if the sequence encoding HMRP is inserted within a marker gene sequence, transformed cells containing sequences encoding HMRP can be identified by the absence of marker gene function. Alternatively, a marker gene can be placed in tandem with a sequence encoding HMRP under the control of a single promoter. Expression of the marker gene in response to induction or selection usually indicates expression of the tandem gene as well.

Alternatively, host cells which contain the nucleic acid sequence encoding HMRP and express HMRP may be identified by a variety of procedures known to those of skill in the art. These procedures include, but are not limited to, DNA-DNA or DNA-RNA hybridizations and protein bioassay or immunoassay techniques which include membrane, solution, or chip based technologies for the detection and/or quantification of nucleic acid or protein sequences.

The presence of polynucleotide sequences encoding HMRP can be detected by DNA-DNA or DNA-RNA hybridization or amplification using probes or fragments or fragments of polynucleotides encoding HMRP. Nucleic acid amplification based assays involve the use of oligonucleotides or oligomers based on the sequences encoding HMRP to detect transformants containing DNA or RNA encoding HMRP.

A variety of protocols for detecting and measuring the expression of HMRP, using either polyclonal or monoclonal antibodies specific for the protein, are known in the art. Examples of such techniques include enzyme-linked immunosorbent assays (ELISAs), radioimmunoassays (RIAs), and fluorescence activated cell sorting (FACS). A two-site, monoclonal-based immunoassay utilizing monoclonal antibodies reactive to two non-interfering epitopes on HMRP is preferred, but a competitive binding assay may be employed. These and other assays are well described in the art. (See, e.g., Hampton, R. et al. (1990) *Serological Methods, a Laboratory Manual,* APS Press, St Paul, Minn., Section IV; and Maddox, D. E. et al. (1983) J. Exp. Med. 158:1211–1216).

A wide variety of labels and conjugation techniques are known by those skilled in the art and may be used in various nucleic acid and amino acid assays. Means for producing labeled hybridization or PCR probes for detecting sequences related to polynucleotides encoding HMRP include oligolabeling, nick translation, end-labeling, or PCR amplification using a labeled nucleotide. Alternatively, the sequences encoding HMRP, or any fragments thereof, may be cloned into a vector for the production of an mRNA probe. Such vectors are known in the art, are commercially available, and may be used to synthesize RNA probes in vitro by addition of an appropriate RNA polymerase such as T7, T3, or SP6 and labeled nucleotides. These procedures may be conducted using a variety of commercially available kits, such as those provided by Pharmacia & Upjohn (Kalamazoo, Micg.), Promega (Madison, Wis.), and U.S. Biochemical Corp. (Cleveland, Ohio). Suitable reporter molecules or labels which may be used for ease of detection include radionuclides, enzymes, fluorescent, chemiluminescent, or chromogenic agents, as well as substrates, cofactors, inhibitors, magnetic particles, and the like.

Host cells transformed with nucleotide sequences encoding HMRP may be cultured under conditions suitable for the expression and recovery of the protein from cell culture. The protein produced by a transformed cell may be secreted or contained intracellularly depending on the sequence and/or the vector used. As will be understood by those of skill in the art, expression vectors containing polynucleotides which encode HMRP may be designed to contain signal sequences which direct secretion of HMRP through a prokaryotic or eukaryotic cell membrane. Other constructions may be used to join sequences encoding HMRP to nucleotide sequences encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp., Seattle, Wash.). The inclusion of cleavable linker sequences, such as those specific for Factor XA or enterokinase (Invitrogen, San Diego, Calif.), between the purification domain and the HMRP encoding sequence may be used to facilitate purification. One such expression vector provides for expression of a fusion protein containing HMRP and a nucleic acid encoding 6 histidine residues preceding a thioredoxin or an enterokinase cleavage site. The histidine residues facilitate purification on immobilized metal ion affinity chromatography. (IMIAC) (See, e.g., Porath, J. et al. (1992) Prot. Exp. Purif. 3: 263–281.) The enterokinase cleavage site provides a means for purifying HMRP from the fusion protein. (See, e.g., Kroll, D. J. et al. (1993) DNA Cell Biol. 12:441–453.)

Fragments of HMRP may be produced not only by recombinant production, but also by direct peptide synthesis using solid-phase techniques. (See, e.g., Merrifield, J. (1963) J. Am. Chem. Soc. 85:2149–2154.) Protein synthesis may be performed by manual techniques or by automation. Automated synthesis may be achieved, for example, using the Applied Biosystems 431 A peptide synthesizer (Perkin Elmer). Various fragments of HMRP may be synthesized separately and then combined to produce the full length molecule.

Therapeutics

Chemical and structural homology exists between HMRP and rat SCAMP 37 (GI 487057). In addition, HMRP is widely expressed in proliferating tissues and in tissues associated with the immune system. Therefore, HMRP appears to play a role in neurological, endocrine, immunological and cell proliferative disorders.

Therefore, in one embodiment, HMRP or a fragment or derivative thereof may be administered to a subject to treat or prevent a neurological disorder. Such disorders can include, but are not limited to, akathesia, Alzheimer's disease, amnesia, amyotrophic lateral sclerosis, bipolar disorder, catatonia, cerebral neoplasms, dementia, depression, diabetic neuropathy, Down's syndrome, tardive dyskinesia, dystonias, epilepsy, Huntington's disease, multiple sclerosis, neurofibromatosis, Parkinson's disease, paranoid psychoses, postherpetic neuralgia, schizophrenia, and Tourette's disorder.

In another embodiment, a vector capable of expressing HMRP or a fragment or derivative thereof may be administered to a subject to treat or prevent a neurological disorder including, but not limited to, those described above.

In a further embodiment, a pharmaceutical composition comprising a substantially purified HMRP in conjunction with a suitable pharmaceutical carrier may be administered to a subject to treat or prevent a neurological disorder including, but not limited to, those provided above.

In still another embodiment, an agonist which modulates the activity of HMRP may be administered to a subject to treat or prevent a neurological disorder including, but not limited to, those listed above.

In another embodiment, HMRP or a fragment or derivative thereof may be administered to a subject to treat or prevent an endocrine disorder. Such disorders can include, but are not limited to, Addison's disease, carcinoid syndrome, Cushing's disease, diabetes insipidus, diabetes mellitus, hyperaldosteronism, hyper- and hypoglycemia, goiter, Grave's disease, multiple endocrine neoplasia syndromes, pheochromocytoma, polyendocrine deficiency syndromes, and thryoiditis.

In another embodiment, a vector capable of expressing HMRP or a fragment or derivative thereof may be administered to a subject to treat or prevent an endocrine disorder including, but not limited to, those described above.

In a further embodiment, a pharmaceutical composition comprising a substantially purified HMRP in conjunction with a suitable pharmaceutical carrier may be administered to a subject to treat or prevent an endocrine disorder including, but not limited to, those provided above.

In still another embodiment, an agonist which modulates the activity of HMRP may be administered to a subject to treat or prevent an endocrine disorder including, but not limited to, those listed above.

In another embodiment, HMRP or a fragment or derivative thereof may be administered to a subject to treat or prevent an immunological disorder. Such disorders can include, but are not limited to, AIDS, Addison's disease, adult respiratory distress syndrome, allergies, ankylosing spondylitis, amyloidosis, anemia, asthma, atherosclerosis, autoimmune hemolytic anemia, autoimmune thyroiditis, bronchitis, cholecystitis, contact dermayitis, Crohn's disease, atopic dermatitis, dermatomyositis, diabetes mellitus, emphysema, erythema nodosum, atrophic gastritis, glomerulonephritis, Goodpasture's syndrome, gout, Graves' disease, Hashimoto's thyroiditis, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, systemic anaphylaxis, systemic lupus erythematosus, systemic sclerosis, ulcerative colitis, Werner syndrome, and complications of cancer, hemodialysis, and extracorporeal circulation; viral, bacterial, fungal, parasitic, protozoal, and helminthic infections; and trauma.

In another embodiment, a vector capable of expressing HMRP or a fragment or derivative thereof may be administered to a subject to treat or prevent an immunological disorder including, but not limited to, those described above.

In a further embodiment, a pharmaceutical composition comprising a substantially purified HMRP in conjunction with a suitable pharmaceutical carrier may be administered to a subject to treat or prevent an immunological disorder including, but not limited to, those provided above.

In still another embodiment, an agonist which modulates the activity of HMRP may be administered to a subject to treat or prevent an immunological disorder including, but not limited to, those listed above.

In a further embodiment, an antagonist of HMRP may be administered to a subject to treat or prevent a cell proliferative disorder. Such disorders may include, but are not limited to, arteriosclerosis, atherosclerosis, bursitis, cirrhosis, hepatitis, mixed connective tissue disease (MCTD), myelofibrosis, paroxysmal nocturnal hemoglobinuria, polycythemia vera, psoriasis, primary thrombocythemia, and cancers including adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. In one aspect, an antibody which specifically binds HMRP may be used directly as an antagonist or indirectly as a targeting or delivery mechanism for bringing a pharmaceutical agent to cells or tissue which express HMRP.

In an additional embodiment, a vector expressing the complement of the polynucleotide encoding HMRP may be administered to a subject to treat or prevent a cell proliferative disorder including, but not limited to, those described above.

In other embodiments, any of the proteins, antagonists, antibodies, agonists, complementary sequences, or vectors of the invention may be administered in combination with other appropriate therapeutic agents. Selection of the appropriate agents for use in combination therapy may be made by one of ordinary skill in the art, according to conventional pharmaceutical principles. The combination of therapeutic agents may act synergistically to effect the treatment or prevention of the various disorders described above. Using this approach, one may be able to achieve therapeutic efficacy with lower dosages of each agent, thus reducing the potential for adverse side effects.

An antagonist of HMRP may be produced using methods which are generally known in the art. In particular, purified HMRP may be used to produce antibodies or to screen libraries of pharmaceutical agents to identify those which specifically bind HMRP. Antibodies to HMRP may also be generated using methods that are well known in the art. Such antibodies may include, but are not limited to, polyclonal, monoclonal, chimeric, and single chain antibodies, Fab fragments, and fragments produced by a Fab expression library. Neutralizing antibodies (i.e., those which inhibit dimer formation) are especially preferred for therapeutic use.

For the production of antibodies, various hosts including goats, rabbits, rats, mice, humans, and others may be immunized by injection with HMRP or with any fragment or oligopeptide thereof which has immunogenic properties. Depending on the host species, various adjuvants may be used to increase immunological response. Such adjuvants include, but are not limited to, Freund's, mineral gels such as aluminum hydroxide, and surface active substances such as lysolecithin, pluronic polyols, polyanions, peptides, oil emulsions, KLH, and dinitrophenol. Among adjuvants used in humans, BCG (bacilli Calmette-Guerin) and *Corynebacterium parvum* are especially preferable.

It is preferred that the oligopeptides, peptides, or fragments used to induce antibodies to HMRP have an amino acid sequence consisting of at least about 5 amino acids, and, more preferably, of at least about 10 amino acids. It is also preferable that these oligopeptides, peptides, or fragments are identical to a portion of the amino acid sequence of the natural protein and contain the entire amino acid sequence of a small, naturally occurring molecule. Short stretches of HMRP amino acids may be fused with those of another protein, such as KLH, and antibodies to the chimeric molecule may be produced.

Monoclonal antibodies to HMRP may be prepared using any technique which provides for the production of antibody molecules by continuous cell lines in culture. These include, but are not limited to, the hybridoma technique, the human B-cell hybridoma technique, and the EBV-hybridoma technique. (See, e.g., Kohler, G. et al. (1975) Nature 256:495–497; Kozbor, D. et al. (1985) J. Immunol. Methods 81:31–42; Cote, R. J. et al. (1983) Proc. Natl. Acad. Sci. 80:2026–2030; and Cole, S. P. et al. (1984) Mol. Cell Biol. 62:109–120.)

In addition, techniques developed for the production of "chimeric antibodies," such as the splicing of mouse antibody genes to human antibody genes to obtain a molecule with appropriate antigen specificity and biological activity, can be used. (See, e.g., Morrison, S. L. et al. (1984) Proc. Natl. Acad. Sci. 81:6851–6855; Neuberger, M. S. et al. (1984) Nature 312:604–608; and Takeda, S. et al. (1985) Nature 314:452–454.) Alternatively, techniques described for the production of single chain antibodies may be adapted, using methods known in the art, to produce HMRP-specific single chain antibodies. Antibodies with related specificity, but of distinct idiotypic composition, may be generated by chain shuffling from random combinatorial immunoglobulin libraries. (See, e.g., Burton D. R. (1991) Proc. Natl. Acad. Sci. 88:11120–11123.)

Antibodies may also be produced by inducing in vivo production in the lymphocyte population or by screening immunoglobulin libraries or panels of highly specific binding reagents as disclosed in the literature. (See, e.g., Orlandi, R. et al. (1989) Proc. Natl. Acad. Sci. 86: 3833–3837; and Winter, G. et al. (1991) Nature 349:293–299.)

Antibody fragments which contain specific binding sites for HMRP may also be generated. For example, such fragments include, but are not limited to, F(ab')2 fragments produced by pepsin digestion of the antibody molecule and Fab fragments generated by reducing the disulfide bridges of the F(ab')2 fragments. Alternatively, Fab expression libraries may be constructed to allow rapid and easy identification of monoclonal Fab fragments with the desired specificity. (See, e.g., Huse, W. D. et al. (1989) Science 254:1275–1281.)

Various immunoassays may be used for screening to identify antibodies having the desired specificity. Numerous protocols for competitive binding or immunoradiometric assays using either polyclonal or monoclonal antibodies with established specificities are well known in the art. Such immunoassays typically involve the measurement of complex formation between HMRP and its specific antibody. A two-site, monoclonal-based immunoassay utilizing monoclonal antibodies reactive to two non-interfering HMRP epitopes is preferred, but a competitive binding assay may also be employed. (Maddox, supra.)

In another embodiment of the invention, the polynucleotides encoding HMRP, or any fragment or complement thereof, may be used for therapeutic purposes. In one aspect, the complement of the polynucleotide encoding HMRP may be used in situations in which it would be desirable to block the transcription of the mRNA. In particular, cells may be transformed with sequences complementary to polynucleotides encoding HMRP. Thus, complementary molecules or fragments may be used to modulate HMRP activity, or to achieve regulation of gene function. Such technology is now well known in the art, and sense or antisense oligonucleotides or larger fragments can be designed from various locations along the coding or control regions of sequences encoding HMRP.

Expression vectors derived from retroviruses, adenoviruses, or herpes or vaccinia viruses, or from various bacterial plasmids, may be used for delivery of nucleotide sequences to the targeted organ, tissue, or cell population. Methods which are well known to those skilled in the art can be used to construct vectors which will express nucleic acid sequence complementary to the polynucleotides of the gene encoding HMRP. (See, e.g., Sambrook, supra; and Ausubel, supra.)

Genes encoding HMRP can be turned off by transforming a cell or tissue with expression vectors which express high levels of a polynucleotide or fragment thereof encoding HMRP. Such constructs may be used to introduce untranslatable sense or antisense sequences into a cell. Even in the absence of integration into the DNA, such vectors may continue to transcribe RNA molecules until they are disabled by endogenous nucleases. Transient expression may last for a month or more with a non-replicating vector, and may last even longer if appropriate replication elements are part of the vector system.

As mentioned above, modifications of gene expression can be obtained by designing complementary sequences or antisense molecules (DNA, RNA, or PNA) to the control, 5', or regulatory regions of the gene encoding HMRP. Oligonucleotides derived from the transcription initiation site, e.g., between about positions −10 and +10 from the start site, are preferred. Similarly, inhibition can be achieved using triple helix base-pairing methodology. Triple helix pairing is useful because it causes inhibition of the ability of the double helix to open sufficiently for the binding of polymerases, transcription factors, or regulatory molecules. Recent therapeutic advances using triplex DNA have been described in the literature. (See, e.g., Gee, J. E. et al. (1994) in Huber, B. E. and B. I. Carr, *Molecular and Immunologic Approaches*, Futura Publishing Co., Mt. Kisco, N.Y., pp. 163–177.) A complementary sequence or antisense molecule may also be designed to block translation of mRNA by preventing the transcript from binding to ribosomes.

Ribozymes, enzymatic RNA molecules, may also be used to catalyze the specific cleavage of RNA. The mechanism of ribozyme action involves sequence-specific hybridization of the ribozyme molecule to complementary target RNA, followed by endonucleolytic cleavage. For example, engineered hammerhead motif ribozyme molecules specifically and efficiently catalyze endonucleolytic cleavage of sequences encoding HMRP.

Specific ribozyme cleavage sites within any potential RNA target are initially identified by scanning the target molecule for ribozyme cleavage sites, including the following sequences: GUA, GUU, and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Complementary ribonucleic acid molecules and ribozymes of the invention may be prepared by any method known in the art for the synthesis of nucleic acid molecules. These include techniques for chemically synthesizing oligonucleotides such as solid phase phosphoramidite chemical synthesis. Alternatively, RNA molecules may be generated by in vitro and in vivo transcription of DNA sequences encoding HMRP. Such DNA sequences may be incorporated into a wide variety of vectors with suitable RNA polymerase promoters such as T7 or SP6. Alternatively, these cDNA constructs that synthesize complementary RNA constitutively or inducibly can be introduced into cell lines, cells, or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine, and wybutosine, as well as acetyl-, methyl-, thio-, and similarly modified forms of adenine, cytidine, guanine, thymine, and uridine which are not as easily recognized by endogenous endonucleases.

Many methods for introducing vectors into cells or tissues are available and equally suitable for use in vivo, in vitro, and ex vivo. For ex vivo therapy, vectors may be introduced into stem cells taken from the patient and clonally propagated for autologous transplant back into that same patient. Delivery by transfection, by liposome injections, or by polycationic amino polymers may be achieved using methods which are well known in the art. (See, e.g., Goldman, C. K. et al. (1997) Nature Biotechnology 15:462–466.)

Any of the therapeutic methods described above may be applied to any subject in need of such therapy, including, for example, mammals such as dogs, cats, cows, horses, rabbits, monkeys, and most preferably, humans.

An additional embodiment of the invention relates to the administration of a pharmaceutical or sterile composition, in conjunction with a pharmaceutically acceptable carrier, for any of the therapeutic effects discussed above. Such pharmaceutical compositions may consist of HMRP, antibodies to HMRP, and mimetics, agonists, antagonists, or inhibitors of HMRP. The compositions may be administered alone or in combination with at least one other agent, such as a stabilizing compound, which may be administered in any sterile, biocompatible pharmaceutical carrier including, but not limited to, saline, buffered saline, dextrose, and water. The compositions may be administered to a patient alone, or in combination with other agents, drugs or hormones.

The pharmaceutical compositions utilized in this invention may be administered by any number of routes including, but not limited to, oral, intravenous, intramuscular, intra-arterial, intramedullary, intrathecal, intraventricular, transdermal, subcutaneous, intraperitoneal, intranasal, enteral, topical, sublingual, or rectal means.

In addition to the active ingredients, these pharmaceutical compositions may contain suitable pharmaceutically acceptable carriers comprising excipients and auxiliaries which facilitate processing of the active compounds into preparations which can be used pharmaceutically. Further details on techniques for formulation and administration may be found in the latest edition of *Remington's Pharmaceutical Sciences* (Maack Publishing Co., Easton, Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions, and the like, for ingestion by the patient.

Pharmaceutical preparations for oral use can be obtained through combining active compounds with solid excipient and processing the resultant mixture of granules (optionally, after grinding) to obtain tablets or dragee cores. Suitable auxiliaries can be added, if desired. Suitable excipients include carbohydrate or protein fillers, such as sugars, including lactose, sucrose, mannitol, and sorbitol; starch from corn, wheat, rice, potato, or other plants; cellulose, such as methyl cellulose, hydroxypropylmethyl-cellulose, or sodium carboxymethylcellulose; gums, including arabic and tragacanth; and proteins, such as gelatin and collagen. If desired, disintegrating or solubilizing agents may be added, such as the cross-linked polyvinyl pyrrolidone, agar, and alginic acid or a salt thereof, such as sodium alginate.

Dragee cores may be used in conjunction with suitable coatings, such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, i.e., dosage.

Pharmaceutical preparations which can be used orally include push-fit capsules made of gelatin, as well as soft, sealed capsules made of gelatin and a coating, such as glycerol or sorbitol. Push-fit capsules can contain active ingredients mixed with fillers or binders, such as lactose or starches, lubricants, such as talc or magnesium stearate, and, optionally, stabilizers. In soft capsules, the active compounds may be dissolved or suspended in suitable liquids, such as fatty oils, liquid, or liquid polyethylene glycol with or without stabilizers.

Pharmaceutical formulations suitable for parenteral administration may be formulated in aqueous solutions, preferably in physiologically compatible buffers such as Hanks' solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils, such as sesame oil, or synthetic fatty acid esters, such as ethyl oleate, triglycerides, or liposomes. Non-lipid polycationic amino polymers may also be used for delivery. Optionally, the suspension may also contain suitable stabilizers or agents to increase the solubility of the compounds and allow for the preparation of highly concentrated solutions.

For topical or nasal administration, penetrants appropriate to the particular barrier to be permeated are used in the formulation. Such penetrants are generally known in the art.

The pharmaceutical compositions of the present invention may be manufactured in a manner that is known in the art, e.g., by means of conventional mixing, dissolving, granulating, dragee-making, levigating, emulsifying, encapsulating, entrapping, or lyophilizing processes.

The pharmaceutical composition may be provided as a salt and can be formed with many acids, including but not limited to, hydrochloric, sulfuric, acetic, lactic, tartaric, malic, and succinic acids. Salts tend to be more soluble in aqueous or other protonic solvents than are the corresponding free base forms. In other cases, the preferred preparation may be a lyophilized powder which may contain any or all of the following: 1 mM to 50 mM histidine, 0.1% to 2% sucrose, and 2% to 7% mannitol, at a pH range of 4.5 to 5.5, that is combined with buffer prior to use.

After pharmaceutical compositions have been prepared, they can be placed in an appropriate container and labeled for treatment of an indicated condition. For administration of HMRP, such labeling would include amount, frequency, and method of administration.

Pharmaceutical compositions suitable for use in the invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays of neoplastic cells, for example, or in animal models, usually mice, rabbits, dogs, or pigs. An animal model may also be used to determine the appropriate concentration range and route of administration. Such information can then be used to determine useful doses and routes for administration in humans.

A therapeutically effective dose refers to that amount of active ingredient, for example HMRP or fragments thereof, antibodies of HMRP, and agonists, antagonists or inhibitors of HMRP, which ameliorates the symptoms or condition. Therapeutic efficacy and toxicity may be determined by standard pharmaceutical procedures in cell cultures or with experimental animals, such as by calculating the ED50 (the dose therapeutically effective in 50% of the population) or LD50 (the dose lethal to 50% of the population) statistics. The dose ratio of topic to therapeutic effects is the therapeutic index, and it can be expressed as the LD50/ED50 ratio. Pharmaceutical compositions which exhibit large therapeutic indices are preferred. The data obtained from cell culture assays and animal studies is used in formulating a range of dosage for human use. The dosage contained in such compositions is preferably within a range of circulating concentrations that include the ED50 with little or no toxicity. The dosage varies within this range depending upon the dosage form employed, the sensitivity of the patient, and the route of administration.

The exact dosage will be determined by the practitioner, in light of factors related to the subject requiring treatment. Dosage and administration are adjusted to provide sufficient levels of the active moiety or to maintain the desired effect. Factors which may be taken into account include the severity of the disease state, the general health of the subject, the age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on the half-life and clearance rate of the particular formulation.

Normal dosage amounts may vary from 0.1 μg to 100,000 μg, up to a total dose of about 1 gram, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides or polypeptides will be specific to particular cells, conditions, locations, etc.

Diagnostics

In another embodiment, antibodies which specifically bind HMRP may be used for the diagnosis of disorders characterized by expression of HMRP, or in assays to monitor patients being treated with HMRP or agonists, antagonists, and inhibitors of HMRP. Antibodies useful for diagnostic purposes may be prepared in the same manner as those described above for therapeutics. Diagnostic assays for HMRP include methods which utilize the antibody and a label to detect HMRP in human body fluids or in extracts of cells or tissues. The antibodies may be used with or without modification, and may be labeled by covalent or non-covalent joining with a reporter molecule. A wide variety of reporter molecules, several of which are described above, are known in the art and may be used.

A variety of protocols for measuring HMRP, including ELISAs, RIAs, and FACS, are known in the art and provide a basis for diagnosing altered or abnormal levels of HMRP expression. Normal or standard values for HMRP expression are established by combining body fluids or cell extracts taken from normal mammalian subjects, preferably human, with antibody to HMRP under conditions suitable for complex formation. The amount of standard complex formation may be quantified by various methods, preferably by photometric means. Quantities of HMRP expressed in subject samples from biopsied tissues are compared with the standard values. Deviation between standard and subject values establishes the parameters for diagnosing disease.

In another embodiment of the invention, the polynucleotides encoding HMRP may be used for diagnostic purposes. The polynucleotides which may be used include oligonucleotide sequences, complementary RNA and DNA molecules, and PNAs. The polynucleotides may be used to detect and quantitate gene expression in biopsied tissues in which expression of HMRP may be correlated with disease. The diagnostic assay may be used to distinguish between absence, presence, and excess expression of HMRP, and to monitor regulation of HMRP levels during therapeutic intervention.

In one aspect, hybridization with PCR probes which are capable of detecting polynucleotide sequences, including genomic sequences, encoding HMRP or closely related molecules may be used to identify nucleic acid sequences which encode HMRP. The specificity of the probe, whether it is made from a highly specific region (e.g., the 5' regulatory region) or from a less specific region (e.g., the 3' coding region), and the stringency of the hybridization or amplification (maximal, high, intermediate, or low), will determine whether the probe identifies only naturally occurring sequences encoding HMRP, alleles, or related sequences.

Probes may also be used for the detection of related sequences, and should preferably contain at least 50% of the nucleotides from any of the HMRP encoding sequences. The hybridization probes of the subject invention may be DNA or RNA and may be derived from the sequences of SEQ ID NO:2 or SEQ ID NO:4 or from genomic sequences including promoter and enhancer elements and introns of the naturally occurring HMRP.

Means for producing specific hybridization probes for DNAs encoding HMRP include the cloning of polynucleotide sequences encoding HMRP or HMRP derivatives into vectors for the production of mRNA probes. Such vectors are known in the art, are commercially available, and may be used to synthesize RNA probes in vitro by means of the addition of the appropriate RNA polymerases and the appropriate labeled nucleotides. Hybridization probes may be labeled by a variety of reporter groups, for example, by radionuclides such as $^{32}$P or $^{35}$S, or by enzymatic labels, such as alkaline phosphatase coupled to the probe via avidin/biotin coupling systems, and the like.

Polynucleotide sequences encoding HMRP may be used for the diagnosis of a disorder associated with expression of HMRP. Examples of such a disorder include, but are not limited to, a neurological disorder such as akathesia, Alzheimer's disease, amnesia, arnyotrophic lateral sclerosis, bipolar disorder, catatonia, cerebral neoplasms, dementia, depression, diabetic neuropathy, Down's syndrome, tardive dyskinesia, dystonias, epilepsy, Huntington's disease, multiple sclerosis, neurofibromatosis, Parkinson's disease, paranoid psychoses, postherpetic neuralgia, schizophrenia, and Tourette's disorder; an endocrine disorder such as Addison's disease, carcinoid syndrome, Cushing's disease, diabetes insipidus, diabetes mellitus, hyperaldosteronism, hyper- and hypoglycemia, goiter, Grave's disease, multiple endocrine neoplasia syndromes, pheochromocytoma, polyendocrine deficiency syndromes, and thryoiditis; an immunological disorder such as AIDS, Addison's disease, adult respiratory distress syndrome, allergies, ankylosing spondylitis, amyloidosis, anemia, asthma, atherosclerosis, autoimmune hemolytic anemia, autoimmune thyroiditis, bronchitis, cholecystitis, contact dermayitis, Crohn's disease, atopic dermatitis, dermatomyositis, diabetes mellitus, emphysema, erythema nodosum, atrophic gastritis, glomerulonephritis, Goodpasture's syndrome, gout, Graves' disease, Hashimoto's thyroiditis, hypereosinophilia, irritable bowel syndrome, lupus erythematosus, multiple sclerosis, myasthenia gravis, myocardial or pericardial inflammation, osteoarthritis, osteoporosis, pancreatitis, polymyositis, rheumatoid arthritis, scleroderma, Sjögren's syndrome, systemic anaphylaxis, systemic lupus erythematosus, systemic sclerosis, ulcerative colitis, Werner syndrome, and complications of cancer, hemodialysis, and extracorporeal circulation; viral, bacterial, fungal, parasitic, protozoal, and helminthic infections; and trauma; and a cell proliferative disorder such as arteriosclerosis, atherosclerosis, bursitis, cirrhosis, hepatitis, mixed connective tissue disease (MCTD), myelofibrosis, paroxysmal nocturnal hemoglobinuria, polycythemia vera, psoriasis, primary thrombocythemia, and cancers including adenocarcinoma, leukemia, lymphoma, melanoma, myeloma, sarcoma, teratocarcinoma, and, in particular, cancers of the adrenal gland, bladder, bone, bone marrow, brain, breast, cervix, gall bladder, ganglia, gastrointestinal tract, heart, kidney, liver, lung, muscle, ovary, pancreas, parathyroid, penis, prostate, salivary glands, skin, spleen, testis, thymus, thyroid, and uterus. The polynucleotide sequences encoding HMRP may be used in Southern or northern analysis, dot blot, or other membrane-based technologies; in PCR technologies; in dipstick, pin, and ELISA assays; and in microarrays utilizing fluids or tissues from patient biopsies to detect altered HMRP expression. Such qualitative or quantitative methods are well known in the art.

In a particular aspect, the nucleotide sequences encoding HMRP may be useful in assays that detect the presence of associated disorders, particularly those mentioned above.

The nucleotide sequences encoding HMRP may be labeled by standard methods and added to a fluid or tissue sample from a patient under conditions suitable for the formation of hybridization complexes. After a suitable incubation period, the sample is washed and the signal is quantitated and compared with a standard value. If the amount of signal in the patient sample is significantly altered from that of a comparable control sample, the nucleotide sequences have hybridized with nucleotide sequences in the sample, and the presence of altered levels of nucleotide sequences encoding HMRP in the sample indicates the presence of the associated disorder. Such assays may also be used to evaluate the efficacy of a particular therapeutic treatment regimen in animal studies, in clinical trials, or in monitoring the treatment of an individual patient.

In order to provide a basis for the diagnosis of a disorder associated with expression of HMRP, a normal or standard profile for expression is established. This may be accomplished by combining body fluids or cell extracts taken from normal subjects, either animal or human, with a sequence, or a fragment thereof, encoding HMRP, under conditions suitable for hybridization or amplification. Standard hybridization may be quantified by comparing the values obtained from normal subjects with values from an experiment in which a known amount of a substantially purified polynucleotide is used. Standard values obtained from normal samples may be compared with values obtained from samples from patients who are symptomatic for a disorder. Deviation from standard values is used to establish the presence of a disorder.

Once the presence of a disorder is established and a treatment protocol is initiated, hybridization assays may be repeated on a regular basis to evaluate whether the level of expression in the patient begins to approximate that which is observed in the normal subject. The results obtained from successive assays may be used to show the efficacy of treatment over a period ranging from several days to months.

With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Additional diagnostic uses for oligonucleotides designed from the sequences encoding HMRP may involve the use of PCR. These oligomers may be chemically synthesized, generated enzymatically, or produced in vitro. Oligomers will preferably contain a fragment of a polynucleotide encoding HMRP, or a fragment of a polynucleotide complementary to the polynucleotide encoding HMRP, and will be employed under optimized conditions for identification of a specific gene or condition. Oligomers may also be employed under less stringent conditions for detection or quantitation of closely related DNA or RNA sequences.

Methods which may also be used to quantitate the expression of HMRP include radiolabeling or biotinylating nucleotides, coamplification of a control nucleic acid, and interpolating results from standard curves. (See, e.g., Melby, P. C. et al. (1993) J. Immunol. Methods 159:235–244; and Duplaa, C. et al. (1993) Anal. Biochem. 212:229–236.) The speed of quantitation of multiple samples may be accelerated by running the assay in an ELISA format where the oligomer of interest is presented in various dilutions and a spectrophotometric or colorimetric response gives rapid quantitation.

In further embodiments, oligonucleotides or longer fragments derived from any of the polynucleotide sequences described herein may be used as targets in a microarray. The microarray can be used to monitor the expression level of large numbers of genes simultaneously (to produce a transcript image) and to identify genetic variants, mutations, and polymorphisms. This information may be used in determining gene function, in understanding the genetic basis of a disorder, in diagnosing a disorder, and in developing and monitoring the activities of therapeutic agents.

In one embodiment, the microarray is prepared and used according to methods known in the art. (See, e.g., Chee et al. (1995) PCT application W095/11995; Lockhart, D. J. et al. (1996) Nat. Biotech. 14:1675–1680; and Schena, M. et al. (1996) Proc. Natl. Acad. Sci. 93:10614–10619.)

The microarray is preferably composed of a large number of unique single-stranded nucleic acid sequences, usually either synthetic antisense oligonucleotides or fragments of cDNAs, fixed to a solid support. The oligonucleotides are preferably about 6 to 60 nucleotides in length, more preferably about 15 to 30 nucleotides in length, and most preferably about 20 to 25 nucleotides in length. For a certain type of microarray, it may be preferable to use oligonucleotides which are about 7 to 10 nucleotides in length. The microarray may contain oligonucleotides which cover the known 5' or 3' sequence, or may contain sequential oligonucleotides which cover the full length sequence or unique oligonucleotides selected from particular areas along the length of the sequence. Polynucleotides used in the microarray may be oligonucleotides specific to a gene or genes of interest in which at least a fragment of the sequence is known or oligonucleotides specific to one or more unidentified cDNAs common to a particular cell or tissue type or to a normal, developmental, or disease state. In certain situations, it may be appropriate to use pairs of oligonucleotides on a microarray. The pairs will be identical, except for one nucleotide preferably located in the center of the sequence. The second oligonucleotide in the pair (mismatched by one) serves as a control. The number of oligonucleotide pairs may range from about 2 to 1,000,000.

In order to produce oligonucleotides to a known sequence for a microarray, the gene of interest is examined using a computer algorithm which starts at the 5' end, or, more preferably, at the 3' end of the nucleotide sequence. The algorithm identifies oligomers of defined length that are unique to the gene, have a GC content within a range suitable for hybridization, and lack predicted secondary structure that may interfere with hybridization. In one aspect, the oligomers are synthesized at designated areas on a substrate using a light-directed chemical process. The substrate may be paper, nylon, any other type of membrane, filter, chip, glass slide, or any other suitable solid support.

In one aspect, the oligonucleotides may be synthesized on the surface of the substrate by using a chemical coupling procedure and an ink jet application apparatus. (See, e.g., Baldeschweiler et al. (1995) PCT application WO95/251116.) In another aspect, a grid array analogous to a dot or slot blot (HYBRIDOT apparatus, GIBCO/BRL) may be used to arrange and link cDNA fragments or oligonucleotides to the surface of a substrate using a vacuum system or thermal, UV, mechanical or chemical bonding procedures. In yet another aspect, an array may be produced by hand or by using available devices, materials, and machines (including BRINKMAN multichannel pipettors or robotic instruments), and may contain 8, 24, 96, 384, 1536, or 6144 oligonucleotides, or any other multiple from 2 to 1,000,000 which lends itself to the efficient use of commercially available instrumentation.

In order to conduct sample analysis using the microarrays, polynucleotides are extracted from a biological sample. The biological samples may be obtained from any bodily fluid (blood, urine, saliva, phlegm, gastric juices, etc.), cultured cells, biopsies, or other tissue preparations. To produce probes, the polynucleotides extracted from the sample are used to produce nucleic acid sequences which are complementary to the nucleic acids on the microarray. If the microarray consists of cDNAs, antisense RNAs (aRNA) are appropriate probes. Therefore, in one aspect, mRNA is used to produce cDNA which, in turn and in the presence of fluorescent nucleotides, is used to produce fragment or oligonucleotide aRNA probes. These fluorescently labeled probes are incubated with the microarray so that the probe sequences hybridize to the cDNA oligonucleotides of the microarray. In another aspect, nucleic acid sequences used as probes can include polynucleotides, fragments, and complementary or antisense sequences produced using restriction enzymes, PCR technologies, and Oligolabeling or TransProbe kits (Pharmacia & Upjohn) well known in the area of hybridization technology.

Incubation conditions are adjusted so that hybridization occurs with precise complementary matches or with various degrees of less complementarity. After removal of nonhybridized probes, a scanner is used to determine the levels and patterns of fluorescence. The scanned images are examined to determine the degree of complementarity and the relative abundance of each oligonucleotide sequence on the microarray. A detection system may be used to measure the absence, presence, and amount of hybridization for all of the distinct sequences simultaneously. This data may be used for large scale correlation studies or for functional analysis of the sequences, mutations, variants, or polymorphisms among samples. (See, e.g., Heller, R. A. et al. (1997) Proc. Natl. Acad. Sci. 94:2150–2155.)

In another embodiment of the invention, nucleic acid sequences encoding HMRP may be used to generate hybridization probes useful for mapping the naturally occurring genomic sequence. The sequences may be mapped to a particular chromosome, to a specific region of a chromosome, or to artificial chromosome constructions, such as human artificial chromosomes (HACs), yeast artificial chromosomes (YACs), bacterial artificial chromosomes (BACs), bacterial P1 constructions, or single chromosome cDNA libraries. (See, e.g., Price, C. M. (1993) Blood Rev. 7:127–134; and Trask, B. J. (1991) Trends Genet.

Fluorescent in situ hybridization (FISH) may be correlated with other physical chromosome mapping techniques and genetic map data. (See, e.g., Heinz-Ulrich, et al. (1995) in Meyers, R. A. (ed.) *Molecular Biology and Biotechnology*, VCH Publishers New York, N.Y., pp. 965–968.) Examples of genetic map data can be found in various scientific journals or at the Online Mendelian Inheritance in Man (OMIM) site. Correlation between the location of the gene encoding HMRP on a physical chromosomal map and a specific disorder, or predisposition to a specific disorder, may help define the region of DNA associated with that disorder. The nucleotide sequences of the subject invention may be used to detect differences in gene sequences between normal, carrier, and affected individuals.

In situ hybridization of chromosomal preparations and physical mapping techniques, such as linkage analysis using established chromosomal markers, may be used for extending genetic maps. Often the placement of a gene on the chromosome of another mammalian species, such as mouse, may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once the disease or syndrome has been crudely localized by genetic linkage to a particular genomic region, e.g., AT to 11q22-23, any sequences mapping to that area may represent associated or regulatory genes for further investigation. (See, e.g., Gatti, R. A. et al. (1988) Nature 336:577–580.) The nucleotide sequence of the subject invention may also be used to detect differences in the chromosomal location due to translocation, inversion, etc., among normal, carrier, or affected individuals.

In another embodiment of the invention, HMRP, its catalytic or immunogenic fragments, or oligopeptides thereof can be used for screening libraries of compounds in any of a variety of drug screening techniques. The fragment employed in such screening may be free in solution, affixed to a solid support, borne on a cell surface, or located intracellularly. The formation of binding complexes between HMRP and the agent being tested may be measured.

Another technique for drug screening which may be used provides for high throughput screening of compounds having suitable binding affinity to the protein of interest. (See, e.g., Geysen, et al. (1984) PCT application WO84/03564.) In this method, large numbers of different small test compounds are synthesized on a solid substrate, such as plastic pins or some other surface. The test compounds are reacted with HMRP, or fragments thereof, and washed. Bound HMRP is then detected by methods well known in the art. Purified HMRP can also be coated directly onto plates for use in the aforementioned drug screening techniques. Alternatively, non-neutralizing antibodies can be used to capture the peptide and immobilize it on a solid support.

In another embodiment, one may use competitive drug screening assays in which neutralizing antibodies capable of binding HMRP specifically compete with a test compound for binding HMRP. In this manner, antibodies can be used to detect the presence of any peptide which shares one or more antigenic determinants with HMRP.

In additional embodiments, the nucleotide sequences which encode HMRP may be used in any molecular biology techniques that have yet to be developed, provided the new techniques rely on properties of nucleotide sequences that are currently known, including, but not limited to, such properties as the triplet genetic code and specific base pair interactions.

The examples below are provided to illustrate the subject invention and are not included for the purpose of limiting the invention.

EXAMPLES

I. cDNA Library Construction

TONGTUT01

The TONGTUT01 cDNA library was constructed from tongue tumor tissue removed from a 36-year-old Caucasian male. The frozen tissue was homogenized and lysed in guanidinium isothiocyanate solution using a homogenizer Polytron-PT 3000 (Brinkmann Instruments Inc, Westbury, N.Y.). The lysate was extracted once with phenol, and RNA was isolated according to Stratagene's RNA isolation protocol (Stratagene, La Jolla, Calif.). The RNA was extracted twice with phenol, precipitated with sodium acetate and ethanol, resuspended in RNase-free water, and DNase treated. Poly(A+) RNA was isolated using the OLIGOTX kit (QIAGEN Inc, Chatsworth, Calif.).

Poly(A+) RNA was used to construct the TONGTUT01 cDNA library according to the recommended protocols in the SUPERSCRIPT plasmid system for cDNA synthesis and plasmid cloning (Cat. #18248-013, Gibco/BRL, Gaithersburg, Md.). The cDNAs were fractionated on a SEPHAROSE CL4B column (Cat. #275105-01, Pharmacia, Piscataway, N.J.), and those cDNAs exceeding 400 bp were ligated into the PSPORT1 plasmid (Gibco/BRL). PSPORT1 was subsequently transformed into DH5α competent cells (Cat. #18258-012, Gibco/BRL).

BRSTNOT01

The BRSTNOT01 cDNA library was constructed from breast tissue removed from a 56-year-old Caucasian female who died an accidental death (lot #93032903, Keystone Skin Bank, International Institute for the Advancement of Medicine, Exton, Pa.). The frozen tissue was ground with a mortar and pestle and lysed in guanidinium isothiocyanate solution. The lysate was extracted twice with phenol/chloroform and centrifuged over a CsCl cushion to isolate RNA. The RNA was precipitated with sodium acetate and ethanol, resuspended in RNase-free water, and DNase treated. Poly(A+) RNA was isolated using the OLIGOTEX kit (QIAGEN Inc)

Poly(A+) RNA was used to construct the BRSTNOT01 cDNA library. First strand cDNA synthesis was achieved using an oligo-d(T) primer containing an XhoI restriction site. Second strand synthesis was achieved using a combination of DNA polymerase I, E. coli ligase, and RNase H, followed by the ligation of an EcoRI adaptor to the blunt-ended cDNA. The cDNA was then digested with XhoI restriction enzyme and fractionated on SEPHACRYL S400 (Pharmacia) to obtain sequences that exceeded 1000 bp in size. The size selected cDNAs were inserted into the LAMBDAZAP vector system (Stratagene) and transformed into E. coli strain XL1-BLUEMRF™ (Stratagene).

The PBLUESCRIPT phagemid forms of individual cDNA clones were obtained by the in vivo excision process (Stratagene). The phagemid DNA was purified and used to reinfect fresh host cells (SOLR, Stratagene) to allow recovery of plasmid DNA II Isolation and Sequencing of cDNA Clones

TONGTUT01

Plasmid DNA was released from the cells and purified using the R.E.A.L. PREP 96 plasmid kit (Cat. #26173, QIAGEN Inc.). This kit enabled the simultaneous purification of 96 samples in a 96-well block using multi-channel reagent dispensers. The recommended protocol was employed except for the following changes: I) the bacteria were cultured in 1 ml of sterile Terrific Broth (Cat. #22711, Gibco/BRL) with carbenicillin at 25 mg/L and glycerol at 0.4%; 2) after inoculation, the cultures were incubated for 19 hours and then lysed with 0.3 ml of lysis buffer; and 3) following isopropanol precipitation, the plasmid DNA pellets were each resuspended in 0.1 ml of distilled water. The plasmid DNA samples were stored at 4° C.

The cDNAs were sequenced by the method of Sanger et al. (1975, *J. Mol. Biol.* 94:441f), using a Hamilton MICROLAB 2200 (Hamilton, Reno, Nev.) in combination with peltier thermal cyclers (PTC200 from MJ Research, Watertown, Mass.) and Applied Biosystems 377 DNA sequencing systems.

BRSTNOT01

Plasmid DNA was released from the cells and purified using the MINIPREP kit (Cat. #77468; Advanced Genetic Technologies Corporation, Gaithersburg, Md.). This kit enabled the simultaneous purification of 96 samples in a 96-well block using multi-channel reagent dispensers. The recommended protocol was employed except for the following changes: 1) the bacteria were cultured in 1 ml of sterile Terrific Broth (Cat. #22711, Gibco/BRL) with carbenicillin at 25 mg/L and glycerol at 0.4%; 2) after inoculation, the cultures were incubated for 24 hours and then lysed with 60 µl of lysis buffer; 3) the contents of the block were centrifuged in the Beckman GS-6R (2900 rpm, 5 minutes) before their addition to the primary filter plate; and 4) the addition of isopropanol to TRIS buffer was not routinely performed. After the last step in the protocol, plasmid DNA samples were stored at 4° C.

The cDNAs were sequenced as were the TONGTUT01 cDNAs described above.

III. Homology Searching of cDNA Clones and Their Deduced Proteins

The nucleotide sequences and/or amino acid sequences of the Sequence Listing were used to query sequences in the GenBank, SwissProt, BLOCKS, and Pima II databases. These databases, which contain previously identified and annotated sequences, were searched for regions of homology using BLAST (Basic Local Alignment Search Tool). (See, e.g., Altschul, S. F. (1993) J. Mol. Evol 36:290–300; and Altschul et al. (1990) J. Mol. Biol. 215:403–410.)

BLAST produced alignments of both nucleotide and amino acid sequences to determine sequence similarity. Because of the local nature of the alignments, BLAST was especially useful in determining exact matches or in identifying homologs which may be of prokaryotic (bacterial) or eukaryotic (animal, fungal, or plant) origin. Other algorithms could have been used when dealing with primary sequence patterns and secondary structure gap penalties. (See, e.g., Smith, T. et al. (1992) Protein Engineering 5:35–51.) The sequences disclosed in this application have lengths of at least 49 nucleotides and have no more than 12% uncalled bases (where N is recorded rather than A, C, G, or T).

The BLAST approach searched for matches between a query sequence and a database sequence. BLAST evaluated the statistical significance of any matches found, and reported only those matches that satisfy the user-selected threshold of significance. In this application, threshold was set at $10^{-25}$ for nucleotides and $10^{-10}$ for peptides.

Incyte nucleotide sequences were searched against the GenBank databases for primate (pri), rodent (rod), and other mammalian sequences (mam). Deduced amino acid sequences from the same clones were then searched against GenBank functional protein databases, mammalian (mamp), vertebrate (vrtp), and eukaryote (eukp), for homology.

IV. Northern Analysis

Northern analysis is a laboratory technique used to detect the presence of a transcript of a gene and involves the hybridization of a labeled nucleotide sequence to a membrane on which RNAs from a particular cell type or tissue have been bound. (See, e.g., Sambrook, supra, ch. 7; and Ausubel, F. M. et al. supra, ch. 4 and 16.)

Analogous computer techniques applying BLAST are used to search for identical or related molecules in nucleotide databases such as GenBank or the LIFESEQ database (Incyte Pharmaceuticals). This analysis is much faster than multiple membrane-based hybridizations. In addition, the sensitivity of the computer search can be modified to determine whether any particular match is categorized as exact or homologous.

The basis of the search is the product score, which is defined as:

$$\% \text{ sequence identity} \times \% \text{ maximum BLAST score } 100$$

The product score takes into account both the degree of similarity between two sequences and the length of the sequence match. For example, with a product score of 40, the match will be exact within a 1% to 2% error, and, with a product score of 70, the match will be exact. Homologous molecules are usually identified by selecting those which show product scores between 15 and 40, although lower scores may identify related molecules.

The results of northern analysis are reported as a list of libraries in which the transcript encoding HMRP occurs. Abundance and percent abundance are also reported. Abundance directly reflects the number of times a particular transcript is represented in a cDNA library, and percent abundance is abundance divided by the total number of sequences examined in the cDNA library.

V. Extension of HMRP Encoding Polynucleotides

The nucleic acid sequences of Incyte Clones 980615 and 412453 were used to design oligonucleotide primers for extending partial nucleotide sequences to full length. For each nucleic acid sequence, one primer was synthesized to initiate extension of an antisense polynucleotide strand, and the other was synthesized to initiate extension of a sense polynucleotide strand. Primers were used to facilitate the extension of the known sequence "outward" generating amplicons containing new unknown nucleotide sequence for the region of interest. The initial primers were designed from the cDNA using OLIGO 4.06 software (National Biosciences), or another appropriate program, to be about 22 to 30 nucleotides in length, to have a GC content of about 50% or more, and to anneal to the target sequence at temperatures of about 68° C. to about 72° C. Any stretch of nucleotides which would result in hairpin structures and primer-primer dimerizations was avoided.

Selected human cDNA libraries (GIBCO/BRL) were used to extend the sequence. If more than one extension is necessary or desired, additional sets of primers are designed to further extend the known region.

High fidelity amplification was obtained by following the instructions for the XL-PCR kit (Perkin Elmer) and thoroughly mixing the enzyme and reaction mix. PCR was performed using the Peltier thermal cycler (PTC200; M. J. Research, Watertown, Mass.), beginning with 40 pmol of each primer and the recommended concentrations of all other components of the kit, with the following parameters:

| Step 1  | 94° C. for 1 min (initial denaturation) |
| Step 2  | 65° C. for 1 min |
| Step 3  | 68° C. for 6 min |
| Step 4  | 94° C. for 15 sec |
| Step 5  | 65° C. for 1 min |
| Step 6  | 68° C. for 7 min |
| Step 7  | Repeat steps 4 through 6 for an additional 15 cycles |
| Step 8  | 94° C. for 15 sec |
| Step 9  | 65° C. for 1 min |
| Step 10 | 68° C. for 7:15 min |
| Step 11 | Repeat steps 8 through 10 for an additional 12 cycles |
| Step 12 | 72° C. for 8 min |
| Step 13 | 4° C. (and holding) |

A 5 l to 10 μl aliquot of the reaction mixture was analyzed by electrophoresis on a low concentration (about 0.6% to 0.8%) agarose mini-gel to determine which reactions were successful in extending the sequence. Bands thought to contain the largest products were excised from the gel, purified using QIAQUICK (QIAGEN), and trimmed of overhangs using Klenow enzyme to facilitate religation and cloning.

After ethanol precipitation, the products were redissolved in 13 μl of ligation buffer, 1 μl T4-DNA ligase (15 units) and 1 μl T4 polynucleotide kinase were added, and the mixture was incubated at room temperature for 2 to 3 hours, or overnight at 16° C. Competent E. coli cells (in 40 μl of appropriate media) were transformed with 3 μl of ligation mixture and cultured in 80 μl of SOC medium. (See, e.g., Sambrook, supra, Appendix A, p. 2.) After incubation for one hour at 37° C., the E. coli mixture was plated on Luria Bertani (LB) agar (See, e.g., Sambrook, supra, Appendix A, p. 1) containing 2×Carb. The following day, several colonies were randomly picked from each plate and cultured in 150 μl of liquid LB/2×Carb medium placed in an individual well of an appropriate commercially-available sterile 96-well microtiter plate. The following day, 5 μl of each overnight culture was transferred into a non-sterile 96-well plate and, after dilution 1:10 with water, 5 μl from each sample was transferred into a PCR array.

For PCR amplification, 18 μl of concentrated PCR reaction mix (3.3×) containing 4 units of rTth DNA polymerase, a vector primer, and one or both of the gene specific primers used for the extension reaction were added to each well. Amplification was performed using the following conditions:

| Step 1 | 94° C. for 60 sec |
| Step 2 | 94° C. for 20 sec |
| Step 3 | 55° C. for 30 sec |
| Step 4 | 72° C. for 90 sec |
| Step 5 | Repeat steps 2 through 4 for an additional 29 cycles |
| Step 6 | 72° C. for 180 sec |
| Step 7 | 4° C. (and holding) |

Aliquots of the PCR reactions were run on agarose gels together with molecular weight markers. The sizes of the PCR products were compared to the original partial cDNAs, and appropriate clones were selected, ligated into plasmid, and sequenced.

In like manner, the nucleotide sequences of SEQ ID NO:2 and SEQ ID NO:4 are used to obtain 5' regulatory sequences using the procedure above, oligonucleotides designed for 5' extension, and an appropriate genomic library.

VI. Labeling and Use of Individual Hybridization Probes

Hybridization probes derived from SEQ ID NO:2 and SEQ ID NO:4 are employed to screen cDNAs, genomic DNAs, or mRNAs. Although the labeling of oligonucleotides, consisting of about 20 base pairs, is specifically described, essentially the same procedure is used with larger nucleotide fragments. Oligonucleotides are designed using state-of-the-art software such as OLIGO 4.06 software (National Biosciences) and labeled by combining 50 pmol of each oligomer and 250 μCi of [$\gamma$-$^{32}$P] adenosine triphosphate (Amersham) and T4 polynucleotide kinase (DuPont NEN, Boston, Mass.). The labeled oligonucleotides are substantially purified using a SEPHADEX G-25 superfine resin column (Pharmacia & Upjohn). An aliquot containing $10^7$ counts per minute of the labeled probe is used in a typical membrane-based hybridization analysis of human genomic DNA digested with one of the following endonucleases: Ase I, Bgl II, Eco RI, Pst I, Xba 1, or Pvu II (DuPont NEN).

The DNA from each digest is fractionated on a 0.7 percent agarose gel and transferred to nylon membranes (NYTRAN PLUSE, Schleicher & Schuell, Durham, N.H.). Hybridization is carried out for 16 hours at 40° C. To remove nonspecific signals, blots are sequentially washed at room temperature under increasingly stringent conditions up to 0.1×saline sodium citrate and 0.5% sodium dodecyl sulfate. After XOMAT AR film (Kodak, Rochester, N.Y.) is exposed to the blots, or the bots are exposed in a Phosphoimager cassette (Molecular Dynamics, Sunnyvale, Calif.) hybridization patterns are compared visually.

VII. Microarrays

To produce oligonucleotides for a microarray, one of the nucleotide sequences of the present invention is examined using a computer algorithm which starts at the 3' end of the nucleotide sequence. The algorithm identifies oligomers of defined length that are unique to the gene, have a GC content within a range suitable for hybridization, and lack predicted secondary structure that would interfere with hybridization. The algorithm identifies approximately 20 sequence-specific oligonucleotides of 20 nucleotides in length (20-mers). A matched set of oligonucleotides are created in which one nucleotide in the center of each sequence is altered. This process is repeated for each gene in the microarray, and double sets of twenty 20-mers are synthesized and arranged on the surface of the silicon chip using a light-directed chemical process. (See, e.g., Chee, supra.)

In the alternative, a chemical coupling procedure and an ink jet device are used to synthesize oligomers on the surface of a substrate. (See, e.g., Baldeschweiler, supra.) In another alternative, a grid array analogous to a dot or slot blot is used to arrange and link cDNA fragments or oligonucleotides to the surface of a substrate using a vacuum system or thermal, UV, mechanical, or chemical bonding procedures. A typical array may be produced by hand or using available materials and machines and contain grids of 8 dots, 24 dots, 96 dots, 384 dots, 1536 dots, or 6144 dots. After hybridization, the microarray is washed to remove nonhybridized probes, and a scanner is used to determine the levels and patterns of fluorescence. The scanned image is examined to determine the degree of complementarity and the relative abundance/ expression level of each oligonucleotide sequence in the microarray.

VIII. Complementary Polynucleotides

Sequences complementary to the HMRP-encoding sequences, or any parts thereof, are used to detect, decrease, or inhibit expression of naturally occurring HMRP. Although use of oligonucleotides comprising from about 15 to 30 base pairs is described, essentially the same procedure is used with smaller or with larger sequence fragments. Appropriate oligonucleotides are designed using Oligo 4.06 software and the coding sequence of HMRP. To inhibit transcription, a complementary oligonucleotide is designed from the most unique sequence and used to prevent promoter binding to the coding sequence. To inhibit translation, a complementary oligonucleotide is designed to prevent ribosomal binding to the HMRP-encoding transcript.

IX. Expression of HMRP

Expression of HMRP is accomplished by subcloning the cDNAs into appropriate vectors and transforming the vectors into host cells. In this case, the cloning vector is also used to express HMRP in *E. coli*. This vector contains a promoter for β-galactosidase upstream of the cloning site, followed by sequence containing the amino-terminal Met and the subsequent seven residues of β-galactosidase. Immediately following these eight residues is a bacteriophage promoter useful for transcription and a linker containing a number of unique restriction sites.

Induction of an isolated, transformed bacterial strain with isopropyl beta-D-thiogalactopyranoside (IPTG) using standard methods produces a fusion protein which consists of the first 8 residues of β-galactosidase, about 5 to 15 residues of linker, and the full length protein. The signal residues direct the secretion of HMRP into bacterial growth media which can be used directly in the following assay for activity.

X. Demonstration of HMRP Activity

HMRP activity is measured by the ability of epitope-tagged HMRP to localize to recycling endosomes in African green monkey kidney (Vero) cells. (Wu, T. T. and Castle, J. D. (1997) J. Cell Sci. 110:1533–1541.) In this assay, a DNA sequence encoding the myc epitope tag is inserted in frame into the HMRP cDNA immediately preceding the N-terminal methionine codon using recombinant DNA methods well known in the art. This construct is transfected into Vero cells using an appropriate eukaryotic expression vector. Expressed epitope-tagged HMRP is detected in situ by immunofluorescence microscopy using antibody directed against the myc epitope. The localization of epitope-tagged HMRP reflects that of endogenous HMRP, as previous studies have shown that N-terminal myc epitope-tagged SCAMP 37 colocalizes with endogenous SCAMP-37. (Wu, supra.) Antibody H68.4 directed against human transferrin receptor is used to label recycling endosomes in transfected cells. Co-localization of myc-tagged HMRP and transferrin receptor iz demonstrated by confocal laser scanning microscopy and imaging analysis and is indicative of localization of myc-tagged HMRP to recycling endosomes.

XI. Production of HMRP Specific Antibodies

HMRP substantially purified using PAGE electrophoresis (see, e.g., Harrington, M. G. (1990) Methods Enzymol. 182:488495), or other purification techniques, is used to immunize rabbits and to produce antibodies using standard protocols. The HMRP amino acid sequence is analyzed using DNASTAR software (DNASTAR, Inc.) to determine regions of high immunogenicity, and a corresponding oligopeptide is synthesized and used to raise antibodies by means known to those of skill in the art. Methods for selection of appropriate epitopes, such as those near the C-terminus or in hydrophilic regions are well described in the art. (See, e.g., Ausubel et al. supra, ch. 11.)

Typically, the oligopeptides are 15 residues in length, and are synthesized using an Applied Biosystems 431A peptide synthesizer using fmoc-chemistry and coupled to KLH (Sigma, St. Louis, Mo.) by reaction with N-maleimidobenzoyl-N-hydroxysuccinimide ester (MBS). (See, e.g., Ausubel et al. supra.) Rabbits are immunized with the oligopeptide-KLH complex in complete Freund's adjuvant. Resulting antisera are tested for antipeptide activity, for example, by binding the peptide to plastic, blocking with 1% BSA, reacting with rabbit antisera, washing, and reacting with radio-iodinated goat anti-rabbit IgG.

XII. Purification of Naturally Occurring HMRP Using Specific Antibodies

Naturally occurring or recombinant HMRP is substantially purified by immunoaffinity chromatography using antibodies specific for HMRP. An immunoaffinity column is constructed by covalently coupling HMRP antibody to an activated chromatographic resin, such as CNBr-activated SEPHAROSE (Pharmacia & Upjohn). After the coupling, the resin is blocked and washed according to the manufacturer's instructions.

Media containing HMRP are passed over the immunoaffinity column, and the column is washed under conditions that allow the preferential absorbance of HMRP (e.g., high ionic strength buffers in the presence of detergent). The column is eluted under conditions that disrupt antibody/ HMRP binding (e.g., a buffer of pH 2 to pH 3, or a high concentration of a chaotrope, such as urea or thiocyanate ion), and HMRP is collected.

XIII. Identification of Molecules Which Interact with HMRP

HMRP or biologically active fragments thereof are labeled with $^{125}$I Bolton-Hunter reagent. (See, e.g., Bolton et al. (1973) Biochem. J. 133:529.) Candidate molecules previously arrayed in the wells of a multi-well plate are incubated with the labeled HMRP, washed, and any wells with labeled HMRP complex are assayed. Data obtained using different concentrations of HMRP are used to calculate values for the number, affinity, and association of HMRP with the candidate molecules.

Various modifications and variations of the described methods and systems of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

What is claimed is:

1. A purified polypeptide comprising an amino acid sequence of SEQ ID NO:1 or SEQ ID NO:3.

2. A composition comprising an effective amount of a de of claim 1 and a pharmaceutically acceptable excipient.

* * * * *

UNITED STATES PATENT AND TRADEMARK OFFICE
CERTIFICATE OF CORRECTION

PATENT NO. : 6,235,715 B1
DATED : May 22, 2001
INVENTOR(S) : Lal et al.

It is certified that error appears in the above-identified patent and that said Letters Patent is hereby corrected as shown below:

Column 50,
Claim 2, please replace "de" with -- polypeptide --.

Signed and Sealed this

Twentieth Day of August, 2002

Attest:

Attesting Officer

JAMES E. ROGAN
Director of the United States Patent and Trademark Office

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
        (A) LENGTH: 347 amino acids
        (B) TYPE: amino acid
        (C) STRANDEDNESS: single
        (D) TOPOLOGY: linear (vii) IMMEDIATE SOURCE:
        (A) LIBRARY: TONGTUT01
        (B) CLONE: 980615

(xi) SEQUENCE DESCRIPTION: SEQ ID NO:1:

```
Met Ala Gln Ser Arg Asp Gly Gly Asn Pro Phe Ala Glu Pro Ser Glu
 1               5                  10                  15

Leu Asp Asn Pro Phe Gln Asp Pro Ala Val Ile Gln His Arg Pro Ser
            20                  25                  30

Arg Gln Tyr Ala Thr Leu Asp Val Tyr Asn Pro Phe Glu Thr Arg Glu
        35                  40                  45

Pro Pro Pro Ala Tyr Glu Pro Pro Ala Pro Ala Pro Leu Pro Pro Pro
    50                  55                  60

Ser Ala Pro Ser Leu Gln Pro Ser Arg Lys Leu Ser Pro Thr Glu Pro
65                  70                  75                  80

Lys Asn Tyr Gly Ser Tyr Ser Thr Gln Ala Ser Ala Ala Ala Ala Thr
                85                  90                  95

Ala Glu Leu Leu Lys Lys Gln Glu Glu Leu Asn Arg Lys Ala Glu Glu
            100                 105                 110

Leu Asp Arg Arg Glu Arg Glu Leu Gln His Ala Ala Leu Gly Gly Thr
        115                 120                 125

Ala Thr Arg Gln Asn Asn Trp Pro Pro Leu Pro Ser Phe Cys Pro Val
    130                 135                 140

Gln Pro Cys Phe Phe Gln Asp Ile Ser Met Glu Ile Pro Gln Glu Phe
145                 150                 155                 160

Gln Lys Thr Val Ser Thr Met Tyr Tyr Leu Trp Met Cys Ser Thr Leu
                165                 170                 175

Ala Leu Leu Leu Asn Phe Leu Ala Cys Leu Ala Ser Phe Cys Val Glu
            180                 185                 190

Thr Asn Asn Gly Ala Gly Phe Gly Leu Ser Ile Leu Trp Val Leu Leu
        195                 200                 205

Phe Thr Pro Cys Ser Phe Val Cys Trp Tyr Arg Pro Met Tyr Lys Ala
    210                 215                 220

Phe Arg Ser Asp Ser Ser Phe Asn Phe Phe Val Phe Phe Phe Ile Phe
```

```
225                 230                 235                 240
Phe Val Gln Asp Val Leu Phe Val Leu Gln Ala Ile Gly Ile Pro Gly
                245                 250                 255
Trp Gly Phe Ser Gly Trp Ile Ser Ala Leu Val Val Pro Lys Gly Asn
                260                 265                 270
Thr Ala Val Ser Val Leu Met Leu Leu Val Ala Leu Leu Phe Thr Gly
            275                 280                 285
Ile Ala Val Leu Gly Ile Val Met Leu Lys Arg Ile His Ser Leu Tyr
            290                 295                 300
Arg Arg Thr Gly Ala Ser Phe Gln Lys Ala Gln Glu Phe Ala Ala
305                 310                 315                 320
Gly Val Phe Ser Asn Pro Ala Val Arg Thr Ala Ala Asn Ala Ala
                325                 330                 335
Ala Gly Ala Ala Glu Asn Ala Phe Arg Ala Pro
            340                 345
```

(2) INFORMATION FOR SEQ ID NO:2:

(i) SEQUENCE CHARACTERISTICS:
        (A) LENGTH: 1521 base pairs
        (B) TYPE: nucleic acid
        (C) STRANDEDNESS: single
        (D) TOPOLOGY: linear (vii) IMMEDIATE SOURCE:
        (A) LIBRARY: TONGTUT01
        (B) CLONE: 980615

(xi) SEQUENCE DESCRIPTION: SEQ ID NO:2:

```
NGACGCAGGC GCAACCCACG GCTGCTGCGG GGATCCTTGT GGCCCTTCCG GTCGATGGAA      60
CCAATCCGTG CACAGAGAAG CGGGGCGAAC TGAGGCGAGT GAAGTGGACT CTGAGGGCTA     120
CCGCTACCGC CACTGCTGCG GCAGGGGCGT GGAGGGCAGA GGGCCGCGGA GGCCGCAGTT     180
GCAAACATGG CTCAGAGCAG AGACGGCGGA AACCCGTTCG CCGAGCCCAG CGAGCTTGAC     240
AACCCCTTTC AGGACCCAGC TGTGATCCAG CACCGACCCA GCCGGCAGTA TGCCACGCTT     300
GACGTCTACA ACCCTTTTGA GACCCGGGAG CCACCACCAG CCTATGAGCC TCCAGCCCCT     360
GCCCCATTGC CTCCACCCTC AGCTCCCTCC TTGCAGCCCT CGAGAAAGCT CAGCCCCACA     420
GAACCTAAGA ACTATGGCTC ATACAGCACT CAGGCCTCAG CTGCAGCAGC CACAGCTGAG     480
CTGCTGAAGA AACAGGAGGA GCTCAACCGG AAGGCAGAGG AGTTGGACCG AAGGGAGCGA     540
GAGCTGCAGC ATGCTGCCCT GGGGGGCACA GCTACTCGAC AGAACAATTG CCCCCTCTA     600
CCTTCTTTTT GTCCAGTTCA GCCCTGCTTT TTCCAGGACA TCTCCATGGA GATCCCCCAA     660
GAATTTCAGA AGACTGTATC CACCATGTAC TACCTCTGGA TGTGCAGCAC GCTGGCTCTT     720
CTCCTGAACT TCCTCGCCTG CCTGGCCAGC TTCTGTGTGG AAACCAACAA TGGCGCAGGC     780
TTTGGGCTTT CTATCCTCTG GGTCCTCCTT TTCACTCCCT GCTCCTTTGT CTGCTGGTAC     840
CGCCCCATGT ATAAGGCTTT CCGGAGTGAC AGTTCATTCA ATTTCTTCGT TTTCTTCTTC     900
ATTTTCTTCG TCCAGGATGT GCTCTTTGTC CTCCAGGCCA TTGGTATCCC AGGTTGGGGA     960
TTCAGTGGCT GGATCTCTGC TCTGGTGGTG CCGAAGGGCA ACACAGCAGT ATCCGTGCTC    1020
ATGCTGCTGG TCGCCCTGCT CTTCACTGGC ATTGCTGTGC TAGGAATTGT CATGCTGAAA    1080
CGGATCCACT CCTTATACCG CCGCACAGGT GCCAGCTTTC AGAAGGCCCA GCAAGAATTT    1140
GCTGCTGGTG TCTTCTCCAA CCCTGCGGTG CGAACCGCAG CTGCCAATGC AGCCGCTGGG    1200
GCTGCTGAAA ATGCCTTCCG GGCCCCGTGA CCCCTGACTG GGATGCCCTG GCCCTGCTAC    1260
```

-continued

```
TTGAGGGAGC TGACTTAGCT CCCGTCCCTA AGGTCTCTGG GACTTGGAGA GACATCACTA    1320

ACTGATGGCT CCTCCGTAGT GCTCCCAATC CTATGGCCAT GACTGCTGAA CCTGACAGGC    1380

GTGTGGGGAG TTCACTGTGA CCTAGTCCCC CCATCAGGCC ACACTGCTGC CACCTCTCAC    1440

ACGCCCCAAC CCAGCTTCCC TCTGCTGTGC CACGGCTGTT GCTTCGGTTA TTTAAATAAA    1500

AAGAAAGTGG AACTGGAACT G                                              1521
```

(2) INFORMATION FOR SEQ ID NO:3:

(i) SEQUENCE CHARACTERISTICS:
        (A) LENGTH: 329 amino acids
        (B) TYPE: amino acid
        (C) STRANDEDNESS: single
        (D) TOPOLOGY: linear (vii) IMMEDIATE SOURCE:
        (A) LIBRARY: BRSTNOT01
        (B) CLONE: 412453

(xi) SEQUENCE DESCRIPTION: SEQ ID NO:3:

```
Met Ser Ala Phe Asp Thr Asn Pro Phe Ala Asp Pro Val Asp Val Asn
 1               5                  10                  15

Pro Phe Gln Asp Pro Ser Val Thr Gln Leu Thr Asn Ala Pro Gln Gly
             20                  25                  30

Gly Leu Ala Glu Phe Asn Pro Phe Ser Glu Thr Asn Ala Ala Thr Thr
         35                  40                  45

Val Pro Val Thr Gln Leu Pro Gly Ser Ser Gln Pro Ala Val Leu Gln
     50                  55                  60

Pro Ser Val Glu Pro Thr Gln Pro Thr Pro Gln Ala Val Val Ser Ala
65                  70                  75                  80

Ala Gln Ala Gly Leu Leu Arg Gln Gln Glu Glu Leu Asp Arg Lys Ala
                 85                  90                  95

Ala Glu Leu Glu Arg Lys Glu Arg Glu Leu Gln Asn Thr Val Ala Asn
            100                 105                 110

Leu His Val Arg Gln Asn Asn Trp Pro Pro Leu Pro Ser Trp Cys Pro
        115                 120                 125

Val Lys Pro Cys Phe Tyr Gln Asp Phe Ser Thr Glu Ile Pro Ala Asp
    130                 135                 140

Tyr Gln Arg Ile Cys Lys Met Leu Tyr Tyr Leu Trp Met Leu His Ser
145                 150                 155                 160

Val Thr Leu Phe Leu Asn Leu Leu Ala Cys Leu Ala Trp Phe Ser Gly
                165                 170                 175

Asn Ser Ser Lys Gly Val Asp Phe Gly Leu Ser Ile Leu Trp Phe Leu
            180                 185                 190

Ile Phe Thr Pro Cys Ala Phe Leu Cys Trp Tyr Arg Pro Ile Tyr Lys
        195                 200                 205

Ala Phe Arg Ser Asp Asn Ser Phe Ser Phe Phe Val Phe Phe Phe Val
    210                 215                 220

Phe Phe Cys Gln Ile Gly Ile Tyr Ile Ile Gln Leu Val Gly Ile Pro
225                 230                 235                 240

Gly Leu Gly Asp Ser Gly Trp Ile Ala Ala Leu Ser Thr Leu Asp Asn
                245                 250                 255

His Ser Leu Ala Ile Ser Val Ile Met Met Val Val Ala Gly Phe Phe
            260                 265                 270

Thr Leu Cys Ala Val Leu Ser Val Phe Leu Leu Gln Arg Val His Ser
        275                 280                 285
```

```
Leu Tyr Arg Arg Thr Gly Ala Ser Phe Gln Gln Ala Gln Glu Glu Phe
    290                 295                 300

Ser Gln Gly Ile Phe Ser Ser Arg Thr Phe His Arg Ala Ala Ser Ser
305                 310                 315                 320

Ala Ala Gln Gly Ala Phe Gln Gly Asn
                325

(2) INFORMATION FOR SEQ ID NO:4:

(i) SEQUENCE CHARACTERISTICS:
        (A) LENGTH: 2434 base pairs
        (B) TYPE: nucleic acid
        (C) STRANDEDNESS: single
        (D) TOPOLOGY: linear (vii) IMMEDIATE SOURCE:
        (A) LIBRARY: BRSTNOT01
        (B) CLONE: 412453

(xi) SEQUENCE DESCRIPTION: SEQ ID NO:4:

NCCGGAAGTG GAGGGTCTAC ACGAAGCGCC GCTGGGTCTG GGTGCCCGGA GGCAGCAGCG      60

TTCGCGGAGT TCGCCCGCTG GCCCCCGATC ACCATGTCGG CTTTCGACAC CAACCCCTTC     120

GCGGACCCAG TGGATGTAAA CCCCTTCCAG GATCCCTCTG TGACCCAGCT GACCAACGCC     180

CCGCAGGGCG GCCTGGCGGA ATTCAACCCC TTCTCAGAGA CAAATGCAGC GACAACAGTT     240

CCTGTCACCC AACTCCCTGG GTCCTCACAG CCAGCGGTTC TCCAGCCATC AGTGGAACCA     300

ACCCAGCCGA CCCCCCAGGC CGTGGTGTCT GCAGCCCAGG CAGGCCTGCT CCGGCAGCAG     360

GAAGAACTGG ACAGGAAAGC TGCCGAGCTG AACGCAAGG AGCGGGAGCT GCAGAACACT      420

GTAGCCAACT TGCATGTGAG ACAGAACAAC TGGCCCCCTC TGCCCTCGTG GTGCCCTGTG     480

AAGCCCTGCT TCTATCAGGA TTTCTCCACA GAGATCCCTG CCGACTACCA GCGGATATGC     540

AAGATGCTCT ACTATCTGTG GATGTTGCAT TCAGTGACTC TGTTTCTGAA CCTGCTTGCC     600

TGCCTGGCCT GGTTCTCGGG CAACAGCTCC AAGGGAGTGG ACTTTGGCCT CTCCATCCTG     660

TGGTTTCTGA TCTTCACTCC CTGTGCCTTC CTTTGTTGGT ACCGACCCAT CTATAAGGCC     720

TTTAGGTCCG ACAACTCTTT CAGCTTCTTT GTGTTCTTCT TTGTATTTTT TTGTCAAATA     780

GGGATCTACA TCATCCAGTT GGTTGGCATC CCTGGCCTGG GGACAGCGG TTGGATTGCA      840

GCCCTGTCTA CACTGGATAA TCATTCCCTG GCCATATCAG TCATCATGAT GGTGGTGGCT     900

GGCTTCTTCA CCCTCTGTGC CGTGCTCTCA GTCTTCCTCC TGCAGCGGGT GCACTCCCTC     960

TACCGACGGA CAGGGGCCAG CTTCCAGCAG GCCCAGGAGG AGTTTTCCCA GGGCATCTTC    1020

AGCAGCAGAA CCTTCCACAG AGCTGCTTCA TCTGCTGCCC AAGGAGCCTT CCAGGGGAAT    1080

TAGTCCTCCT CTCTTCTCTC CCCCTCAGCC TTTCTCTCGC CTGCCTTCTG AGCTGCACTT    1140

TCCGTGGGTG CCTTATGTGG TGGTGGTTGT GCCCAGCACA GACCTGGCAG GGTTCTTGCC    1200

GTGGCTCTTC CTCCTCCCTC AGCGACCAGC TCTCCCTGGA ACGGGAGGGA CAGGGAATTT    1260

TTTCCCCCTC TATGTACAAA AAAAAACAAA GCTCTCTTTC CTTCTCTGGT GATGGTTTGG    1320

TAGGATTCTT TTGTCTCTGG AAGCAGTGGG ACTGAAGTTC TCTTCGTCCT GTGCACACAC    1380

AGACACCCCC ACACAGTTGG GATCACAGGC TGACCTGGGC CCATCCCAGC TGGAGCTTTC    1440

TGCCAGGGTC CTGGGCCTTG ACTCCCCCAC CCTGCAGGCC TGGCCTGAAT CTGGCTTCTT    1500

AGACACAGCC CAGTCCTTCC TGCCTGGGCT GGGAATAAGC CTCTCACAGG TTCTGGTGGA    1560

CAGATCTGTT CCCCAGGTCA CTCCAGTGGT CTCCAGGCTT CCAGAGAAGG CTGGTTGCCT    1620
```

-continued

```
CAAGCTCTTC TCTGCCTCAT AAACGGATCC AGAGAAGGCT GGTTGCCTTA AGCTCTTCCC    1680

TGCCTCGTGT TCCTGAGAAA CGGATTAATA GCCCTTTATC CCCCTGCACC CTCCTGCAGG    1740

GGATGGCACT TTGAGCCCTC TGGAGCCCTC CCCTTGCTGA GCCTTACTCT CTTCAGACTT    1800

TCTGAATGTA CAGTGCCGTT GGTTGGGATT TGGGGACTGG AAGGGACCAA GGACACTGAC    1860

CCCAAGCTGT CCTGCCTAGC GTCCAGCGTC TTCTAGGAGG GTGGGGTCTG CCTGTCCTGG    1920

TGTGGTTGGT TTGGCCCTGT TTGCTGTGAC TACCCCCCCC CCTCCCCGAA CCGAGGGACG    1980

GCTGCCTTTG TCTCTGCCTC AGATGCCACC TGCCCCGCCC ATGCTCCCCA TCAGCAGCAT    2040

CCAGACTTTC AGGAAGGGCA GGACCAGCCA GTCCAGAACC GCATCCCTCA GCAGGGACTG    2100

ATAAGCCATC TCTCGGAGGG CCCCCTAATA CCCAGTGGAG TCTGGTTCAC ACCCTGGGGG    2160

GTGTGTCACT GTGATGGGAC ACGTAGGAGT CCACCCTTAA AACCAGCACC CTGTCCCTCG    2220

AGGCTGCCGA GTGGGTGTGT GGACTGGGGT GCCTTCCCAC AAAACTAGCC TCCGGCTCTG    2280

GGCCCGAGAC AGCCGCAGGC CCCAGCCACT GAATGATACT GGCAGCGGCT GGGGTTTTAT    2340

GAACTCCTTT CTGGTATTTT TTCCCCTCTA TGTACAAATG TATATGTTAC GTCTCAATTT    2400

TTGTGCTTAA GTAAAAATAA AAACATTTTC AGAC                              2434
```

(2) INFORMATION FOR SEQ ID NO:5:

(i) SEQUENCE CHARACTERISTICS:
        (A) LENGTH: 338 amino acids
        (B) TYPE: amino acid
        (C) STRANDEDNESS: single
        (D) TOPOLOGY: linear (vii) IMMEDIATE SOURCE:
        (A) LIBRARY: GenBank
        (B) CLONE: 487057

(xi) SEQUENCE DESCRIPTION: SEQ ID NO:5:

```
Met Ser Asp Phe Asp Ser Asn Pro Phe Ala Asp Pro Asp Leu Asn Asn
 1               5                  10                  15

Pro Phe Lys Asp Pro Ser Val Thr Gln Val Thr Arg Asn Val Pro Pro
                20                  25                  30

Gly Leu Asp Glu Tyr Asn Pro Phe Ser Asp Ser Arg Thr Pro Pro Pro
            35                  40                  45

Gly Gly Val Lys Met Pro Asn Val Pro Asn Thr Gln Pro Ala Ile Met
        50                  55                  60

Lys Pro Thr Glu Glu His Pro Ala Tyr Thr Gln Ile Thr Lys Glu His
65                  70                  75                  80

Ala Leu Ala Gln Ala Glu Leu Leu Lys Arg Gln Glu Glu Leu Glu Arg
                85                  90                  95

Lys Ala Ala Glu Leu Asp Arg Arg Glu Arg Glu Met Gln Asn Leu Ser
            100                 105                 110

Gln His Gly Arg Lys Asn Asn Trp Pro Pro Leu Pro Ser Asn Phe Pro
        115                 120                 125

Val Gly Pro Cys Phe Tyr Gln Asp Phe Ser Val Asp Ile Pro Val Glu
    130                 135                 140

Phe Gln Lys Thr Val Lys Leu Met Tyr Tyr Leu Trp Met Phe His Ala
145                 150                 155                 160

Val Thr Leu Phe Leu Asn Ile Phe Gly Cys Leu Ala Trp Phe Cys Val
                165                 170                 175

Asp Ser Ser Arg Ala Val Asp Phe Gly Leu Ser Ile Leu Trp Phe Leu
            180                 185                 190
```

-continued

```
Leu Phe Thr Pro Cys Ser Phe Val Cys Trp Tyr Arg Pro Leu Tyr Gly
            195                 200                 205

Ala Phe Arg Ser Asp Ser Ser Phe Arg Phe Phe Val Phe Phe Phe Val
            210                 215                 220

Tyr Ile Cys Gln Phe Ala Val His Val Leu Gln Ala Ala Gly Phe His
225                 230                 235                 240

Asn Trp Gly Asn Cys Gly Trp Ile Ser Ser Leu Thr Gly Leu Asn Lys
            245                 250                 255

Asn Ile Pro Val Gly Ile Met Met Ile Ile Ile Ala Ala Leu Phe Thr
            260                 265                 270

Ala Ser Ala Val Ile Ser Leu Val Met Phe Lys Lys Val His Gly Leu
            275                 280                 285

Tyr Arg Thr Thr Gly Ala Ser Phe Glu Lys Ala Gln Gln Glu Phe Ala
            290                 295                 300

Thr Gly Val Met Ser Asn Lys Thr Val Gln Thr Ala Ala Ala Asn Ala
305                 310                 315                 320

Ala Ser Thr Ala Ala Thr Ser Ala Ala Gln Asn Ala Phe Lys Gly Asn
            325                 330                 335

Gln Met
```